United States Patent
Harmon et al.

(10) Patent No.: US 12,370,181 B2
(45) Date of Patent: Jul. 29, 2025

(54) REGIMENS OF ESTROGEN RECEPTOR ANTAGONISTS

(71) Applicant: Olema Pharmaceuticals, Inc., San Francisco, CA (US)

(72) Inventors: Cyrus L. Harmon, Bolinas, CA (US); Peter J. Kushner, San Francisco, CA (US); David C. Myles, Berkeley, CA (US); Leslie Hodges Gallagher, Alameda, CA (US); Richard Sun, San Francisco, CA (US)

(73) Assignee: Olema Pharmaceuticals, Inc., San Francisco, CA (US)

( * ) Notice: Subject to any disclaimer, the term of this patent is extended or adjusted under 35 U.S.C. 154(b) by 590 days.

(21) Appl. No.: 17/625,184

(22) PCT Filed: Jul. 6, 2020

(86) PCT No.: PCT/US2020/040863
§ 371 (c)(1),
(2) Date: Jan. 6, 2022

(87) PCT Pub. No.: WO2021/007146
PCT Pub. Date: Jan. 14, 2021

(65) Prior Publication Data
US 2022/0265616 A1 Aug. 25, 2022
US 2023/0109666 A2 Apr. 6, 2023

Related U.S. Application Data

(60) Provisional application No. 62/871,592, filed on Jul. 8, 2019, provisional application No. 62/871,191, filed on Jul. 7, 2019.

(51) Int. Cl.
*A61K 31/437* (2006.01)
*A61K 31/565* (2006.01)
*A61K 45/06* (2006.01)
*A61P 35/00* (2006.01)

(52) U.S. Cl.
CPC .......... *A61K 31/437* (2013.01); *A61K 31/565* (2013.01); *A61K 45/06* (2013.01); *A61P 35/00* (2018.01)

(58) Field of Classification Search
CPC ...... A61K 31/437; A61K 31/565; A61P 35/00
See application file for complete search history.

(56) References Cited

U.S. PATENT DOCUMENTS

| | | |
|---|---|---|
| 4,418,068 A | 11/1983 | Jones |
| 4,659,516 A | 4/1987 | Bowler et al. |
| 5,362,718 A | 11/1994 | Skotnicki et al. |
| 5,393,763 A | 2/1995 | Black et al. |
| 5,457,117 A | 10/1995 | Black et al. |
| 5,478,847 A | 12/1995 | Draper |
| 5,780,497 A | 7/1998 | Miller et al. |
| 5,880,137 A | 3/1999 | Miller et al. |
| 5,998,402 A | 12/1999 | Miller et al. |
| 6,005,102 A | 12/1999 | Raveendranath et al. |
| 6,326,392 B1 | 12/2001 | Gast et al. |
| 6,479,535 B1 | 11/2002 | Pickar et al. |
| 6,512,002 B2 | 1/2003 | Lee et al. |
| 6,583,170 B1 | 6/2003 | Pickar et al. |
| 6,632,834 B2 | 10/2003 | Thompson et al. |
| 6,756,401 B2 | 6/2004 | Day et al. |
| 6,774,122 B2 | 8/2004 | Evans et al. |
| 6,777,424 B2 | 8/2004 | Littman |
| 6,821,989 B2 | 11/2004 | Rosati |
| 6,936,612 B2 | 8/2005 | Barvian et al. |
| 7,456,160 B2 | 11/2008 | Evans et al. |
| 8,227,462 B2 | 7/2012 | Fairhurst et al. |
| 8,299,112 B2 | 10/2012 | Smith et al. |
| 8,455,534 B2 | 6/2013 | Smith et al. |
| 8,703,810 B2 | 4/2014 | Kahraman et al. |
| 8,853,423 B2 | 10/2014 | Govek et al. |
| 9,018,244 B2 | 4/2015 | Kushner et al. |
| 9,078,871 B2 | 7/2015 | Kahraman et al. |
| 9,540,361 B2 | 1/2017 | Dijcks et al. |
| 10,292,971 B2 * | 5/2019 | Myles .................. C07D 471/04 |
| 10,624,878 B2 * | 4/2020 | Myles ..................... A61P 35/00 |
| 11,229,630 B2 | 1/2022 | Myles et al. |

(Continued)

FOREIGN PATENT DOCUMENTS

| | | |
|---|---|---|
| EP | 0705832 A1 | 4/1996 |
| EP | 0802184 A1 | 10/1997 |

(Continued)

OTHER PUBLICATIONS

Alemany, C. et al., A Phase 1/2 Dose Escalation and Expansion Study of OP-1250 in Adults with Advanced and/or Metastatic Hormone Receptor-positive (HR+), HER2-negative (HER2-) Breast Cancer (NCT04505826), presented at AACR-NCI-EORTC Virtual International Conference on Molecular Targets and Cancer Therapeutics on Oct. 7-10, 2021 (11 pages).

Arao, Y and Korach, K. S. et al., The F domain of estrogen receptor a is involved in species-specific, tamoxifen-mediated transactivation, J. Biol. Chem., 293(22):8495-8507 (2018).

Olema Oncology, Complete Estrogen Receptor (ER) Antagonism As An Optimal Approach for ER-Positive Breast Cancer Drug Development, presented at the 2021 JCA-AACR Precision Cancer Medicine International Conference, Sep. 10-12, 2021.

Bardia, A. et al., Evaluation of RAD1901, a novel investigational, selective estrogen receptor degrader (SERD), for the treatment of ER-positive (ER+) advanced breast cancer, Journal of Clinical Oncology, Meeting Abstract presented at the 2017 ASCO Annual Meeting (4 pages).

(Continued)

Primary Examiner — Kevin E Weddington
(74) Attorney, Agent, or Firm — Choate, Hall & Stewart LLP

(57) ABSTRACT

Provided herein are methods of administering estrogen receptor antagonists for use in treatment of cancer. In some embodiments, estrogen receptor antagonists provided herein are tetrahydro pyrido[3,4-b] indole compounds. In some embodiments, provided antagonists are complete estrogen receptor antagonists.

10 Claims, 27 Drawing Sheets

(56) References Cited

U.S. PATENT DOCUMENTS

| | | |
|---|---|---|
| 2001/0056099 A1 | 12/2001 | Day et al. |
| 2002/0013327 A1 | 1/2002 | Lee et al. |
| 2002/0016340 A1 | 2/2002 | Rosati |
| 2002/0128276 A1 | 9/2002 | Day et al. |
| 2005/0272759 A1 | 12/2005 | Moon et al. |
| 2005/0282849 A1 | 12/2005 | Moon et al. |
| 2012/0157402 A1 | 6/2012 | Cao et al. |
| 2012/0238755 A1 | 9/2012 | Ueda et al. |
| 2013/0178445 A1 | 7/2013 | Kushner et al. |
| 2014/0357661 A1 | 12/2014 | Bradbury et al. |
| 2015/0005286 A1 | 1/2015 | Smith et al. |
| 2015/0258080 A1 | 9/2015 | Hager et al. |
| 2016/0175289 A1 | 6/2016 | Labadie et al. |
| 2017/0362228 A1 | 12/2017 | Labadie et al. |
| 2018/0002344 A1 | 1/2018 | Labadie et al. |
| 2018/0214393 A1 | 8/2018 | Hattersley |
| 2018/0235945 A1 | 8/2018 | Labadie et al. |
| 2018/0289679 A1 | 10/2018 | Myles et al. |
| 2019/0247372 A1 | 8/2019 | Myles et al. |
| 2021/0059991 A1 | 3/2021 | Myles et al. |
| 2022/0370421 A1 | 11/2022 | Myles et al. |
| 2023/0129598 A1 | 4/2023 | Harmon et al. |

FOREIGN PATENT DOCUMENTS

| | | |
|---|---|---|
| WO | WO-1999/024027 A2 | 5/1999 |
| WO | WO-2002/003975 A2 | 1/2002 |
| WO | WO-2002/003976 A2 | 1/2002 |
| WO | WO-2002/003977 A2 | 1/2002 |
| WO | WO-2002/003986 A2 | 1/2002 |
| WO | WO-2002/003988 A2 | 1/2002 |
| WO | WO-2002/003989 A2 | 1/2002 |
| WO | WO-2002/003990 A2 | 1/2002 |
| WO | WO-2002/003991 A2 | 1/2002 |
| WO | WO-2002/003992 A2 | 1/2002 |
| WO | WO-2002/004418 A2 | 1/2002 |
| WO | WO-2002/013802 A2 | 2/2002 |
| WO | WO-03/016270 A2 | 2/2003 |
| WO | WO-2005/089764 A1 | 9/2005 |
| WO | WO-2006/078834 A1 | 7/2006 |
| WO | WO-2008/127715 A1 | 10/2008 |
| WO | WO-2010/138695 A1 | 12/2010 |
| WO | WO-2010/138706 A1 | 12/2010 |
| WO | WO-2010/138758 A1 | 12/2010 |
| WO | WO-2011/156518 A2 | 12/2011 |
| WO | WO-2012/084711 A1 | 6/2012 |
| WO | WO-2013/090921 A1 | 6/2013 |
| WO | WO-2014/191726 A1 | 12/2014 |
| WO | WO-2014/203129 A1 | 12/2014 |
| WO | WO-2014/203132 A1 | 12/2014 |
| WO | WO-2014/205136 A1 | 12/2014 |
| WO | WO-2014/205138 A1 | 12/2014 |
| WO | WO-2015/149045 A1 | 10/2015 |
| WO | WO-2016/097072 A1 | 6/2016 |
| WO | WO-2017/059139 A1 | 4/2017 |
| WO | WO-2018/064231 A1 | 4/2018 |
| WO | WO-2018/077630 A1 | 5/2018 |
| WO | WO-2018/197653 A1 | 11/2018 |
| WO | WO-2019/245974 A1 | 12/2019 |
| WO | WO-2020/014435 A1 | 1/2020 |
| WO | WO-2020/014440 A1 | 1/2020 |
| WO | WO-2020/023297 A1 | 1/2020 |
| WO | WO-2020/037203 A2 | 2/2020 |
| WO | WO-2021/007146 A1 | 1/2021 |
| WO | WO-2021/178846 A1 | 9/2021 |

OTHER PUBLICATIONS

Bentrem, D. J. et al, Molecular mechanism of action at estrogen receptor alpha of a new clinically relevant antiestrogen (GW7604) related to tamoxifen, Endocrinology, 142(2): 838-46 (2001).

Blizzard, T.A. et al., Estrogen receptor ligands. Part 14: Application of novel antagonist side chains to existing platforms, Bioorganic & Medicinal Chemistry Letters, 15:5124-5128 (2005).

Cardoso, F. et al., 3rd ESO-ESMO International Consensus Guidelines for Advanced Breast Cancer (ABC 3), Annals of Oncology, 28:16-33 (2017).

Clinical Trials, A Dose Escalation/Expansion Study of Oral OP-1250 in Subjects With Advanced and/or Metastatic HR+, HER2− Breast Cancer, NCT04505826, 4 pages (2022).

Clinical Trials, A Phase 1 Study of Oral OP-1250 in Combination With Palbociclib in HR+/HER2− Breast Cancer Patients, NCT05266105, 7 pages (2022).

Dardes, R. C. et al, Effects of a New Clinically Relevant Antiestrogen (GW5638) Related to Tamoxifen on Breast and Endometrial Cancer Growth in Vivo, Clinical Cancer Research, 8:1995-2001 (2002).

De Savi, C. et al., Optimization of a Novel Binding Motif to (E)-3-(3,5-Difluoro-4-((1R,3R)-2-(2-fluoro-2-methylpropyl)-3-methyl-2,3,4,9-tetrahydro-1 H-pyrido[3,4-b ]indol-1-yl)phenyl)acrylic Acid (AZD9496), a Potent and Orally Bioavailable Selective Estrogen Receptor Downregulator and Antagonist, J. of Med. Chem., 58 (20):8128-8140 (2015).

Dickler, M. et al., Abstract CT231: A first-in-human phase I study to evaluate the oral selective estrogen receptor degrader GDC-0810 (ARN-810) in postmenopausal women with estrogen receptor+ HER2−, advanced/metastatic breast cancer, Cancer Res, 75(Suppl 15):1-4 (2015).

Fan, M. et al, Characterization of molecular and structural determinants of selective estrogen receptor downregulators, Breast Cancer Res. Treat, 103: 37-44 (2007).

Fribbens, C. et al., Plasma ESR1 Mutations and the Treatment of Estrogen Receptor-Positive Advanced Breast Cancer, Journal of Clinical Oncology, 34(25):961-2968 (2020).

Gelsomino, L. et al., ESR1 mutations affect anti-proliferative responses to tamoxifen through enhanced cross-talk with IGF signaling, Breast Cancer Res Treat, 157:253-265 (2016).

Goetz, M., Bringing the Investigational Breast Cancer Drug Endoxifen from Bench to Bedside with NCI Support, National Cancer Institute, 1-7 (2017).

Guan, J. et al., Therapeutic Ligands Antagonize Estrogen Receptor Function by Impairing Its Mobility, Cell, 178: 1-15 (2019).

Hall, J. and McDonnell, D. et al., Coregulators in Nuclear Estrogen Receptor Action, Duke University, Department of Pharmacology and Cancer Biology, 5(6):1-15 (2005).

Hamilton, E. et al., A First-in-Human Study of the New Oral Selective Estrogen Receptor Degrader AZD9496 for ER+/HER2− Advanced Breast Cancer, Clinical Cancer Research, 24(15):1-9 (2018).

Hamilton, E. et al., Abstract #1167, A Phase I/II Open-label, First-in-Human, Multicenter, Dose Escalation and Dose Expansion Study of OP-1250 monotherapy in adult subjects with locally advanced, recurrent, and metastatic Hormone Receptor (HR)-positive, HER2-negative breast cancer (NCT04505826), presented at the San Antonio Breast Cancer Symposium on Dec. 8-11, 2020.

Hamilton, E. et al., Abstract OT-09-10: A phase I/II open-label, first-in-human, multicenter, dose escalation and dose expansion study of OP-1250 monotherapy in adult subjects with advanced and/or metastatic hormone receptor (HR)-positive, HER2-negative breast cancer, Cancer Res., 81(Supp 4):1-5 (2021).

Heldring, N. et al., Estrogen Receptor: How Do They Signal and What Are Their Targets, Physiol. Rev., 87: 905-931 (2007).

Hewitt, S. and Korach, K. S., Estrogen Receptors: New Directions in the New Millennium, Endocr Rev., 39(5):664-675 (2018).

Hodges-Gallagher, L. et al., Abstract #1410: The Complete Estrogen Receptor Antagonist OP-1250 Shrinks Tumors in Xenograft Models and Has Favorable Preclinical Pharmacokinetic Attributes, Olema Oncology, presented at the San Antonio Breast Cancer Symposium on Dec. 8-11, 2020 (1 page).

Hodges-Gallagher, L. et al., Abstract #4376: OP-1250, a complete estrogen receptor antagonist (CERAN) that shrinks estrogen receptor positive tumors and exhibits favorable pharmacokinetics, Cancer Res., 80(Supp 16):1-4 (2020).

Hodges-Gallagher, L. et al., Abstract LB122: The complete estrogen receptor antagonist (Ceran) OP-1250 shrinks ER+ brain metastases

(56) References Cited

OTHER PUBLICATIONS in an intracranial xenograft tumor model expressing mutant ESR1, Cancer Res., 81 (Supp 13):1-4 (2021).

Hodges-Gallagher, L. et al., Abstract P5-05-02: Preclinical development of OP-1250, an oral complete estrogen receptor antagonist (CERAN) that shrinks ER-positive breast tumors in xenograft models, Cancer Res., 80(Supp 4):1-4 (2020).

Hodges-Gallagher, L. et al., Abstract PS18-16: The complete estrogen receptor antagonist OP-1250 shrinks tumors in xenograft models and has favorable preclinical pharmacokinetic attributes, Cancer Res., 81 (Supp 4):1-4 (2021).

Hodges-Gallagher, L. et al., Development of OP-1250, an Oral Complete Estrogen Receptor Antagonist (CERAN) that Shrinks ER-positive Breast Tumors in Xenograft Models, Olema Therapeutics, presented at the San Antonio Breast Cancer Symposium on Dec. 10-14, 2019 (1 page).

Hodges-Gallagher, L. et al., OP-1250 is a Complete Estrogen Receptor Antagonist (CERAN) that Lacks Agonist Activity on Cell Signaling and Proliferation in Breast Cancer Cells, presented at ENA EORTC NCI AACR 32nd Symptosium, San Fransisco (2020).

Hodges-Gallagher, L. et al., OP-1250, a Complete Estrogen Receptor Antagonist (CERAN) that penetrates the brain and prevents lethality from intracranial xenograft tumors expressing mutant ESR1, presented at AACR #4376 (2020).

Hodges-Gallagher, L. et al., Poster OP-1250: A potent orally available complete antagonist of estrogen receptor-mediated signaling that shrinks wild type and mutant breast tumors, European Journal of Cancer, 138S2: S1-S62 (2020).

Hodges-Gallagher, L. et al., The complete estrogen receptor antagonist (Ceran) OP-1250 shrinks ER+ breast cancer tumors expressing the ESR1-Y537S mutant estrogen receptor in an intracranial xenograft model of brain metastases, presented at AACR Annual Meeting #LB122 (2021).

International Search Report for PCT/US2016/054549, 2 pages (Dec. 9, 2016).

International Search Report for PCT/US2020/040863, 4 pages (mailed Oct. 14, 2020).

Jeselsohn, R. et al., ESR1 mutations—a mechanism for acquired endocrine resistance in breast cancer, Nat. Rev. Clin. Oncol. 12, 573-583 (2015).

Jordan, V. C., Antiestrogens and Selective Estrogen Receptor Modulators as Multifunctional Medicines. 1. Receptor Interactions, J. Med. Chem., 46(6): 883-908 (2003).

Jordan, V.C., Alternate antiestrogens and approaches to the prevention of breast cancer, J. Cell Biochem. Suppl., 22:51-7 (1995).

Joseph, J.D. et al., The selective estrogen receptor downregulator GDC-0810 is efficacious in diverse models of ER+ breast cancer, Elife, 5. Pii: 15828 (2016).

Komm, B. S. and Mirkin, S., An overview of current and emerging SERMs, Journal of Steroid Biochemistry and Molecular Bioglogy, 143: 207-222 (2014).

Kumar, V., The estrogen receptor binds tightly to its responsive element as a ligand-induced homodimer, Cell, 55:145-156 (1988).

Lai, A. et al, Identification of GDC-0810 (ARN-810), an Orally Bioavailable Selective Estrogen Receptor Degrader SERD) that Demonstrates Robust Activity in Tamoxifen-Resistant Breast Cancer Xenografts, J. Med Chem., 58(12): 4888-904 (2015).

Laine, M. et al., OP-1250 Prevents Tumor Spread in a Model of Metastatic Mutant ERalpha+ Breast Cancer, presented at American Association for Cancer Research, Apr. 8-13, 2022, New Orleans, LA.

Laxmi, Y. R. S et al., Anti-breast cancer potential of SS1020, a novel antiestrogen lacking estrogenic and genotoxic actions, International Journal of Cancer, 127: 1718-1726 (2010).

Li, S. et al., Endocrine-Therapy-Resistant ESR1 Variants Revealed by Genomic Characterization of Breast-Cancer-Derived Xenografts, Cell Reports, 4:1116-1130 (2013).

Liang, J., Discovery of GNE-149 as a Full Antagonist and Efficient Degrader of Estrogen Receptor alpha for ER+ Breast Cancer, ACS Med. Che. Lett., 11:1342-1347 (2020).

Liu, J. et al., Therapeutic utility of natural estrogen receptor beta agonists on ovarian cancer, Oncotarget, 8(3):50002-50014 (2017).

Lumachi, F. et al., Treatment of Estrogen Receptor-Positive Breast Cancer, Current Medicinal Chemistry, 20: 596-604 (2013).

Mueller, M.D. et al., Regulation of vascular endothelial growth factor (VEGF) gene transcription by estrogen receptors alpha and beta, PNAS, 97(20): 10972-7 (2000).

Nardone, A. et al., The oral selective oestrogen receptor degrader (Serd) AZD9496 is comparable to fulvestrant in antagonising ER and circumventing endocrine resistance, BJC, 120:331-339 (2019).

Nathan, M. R. and Schmid, P., A Review of Fulvestrant in Breast Cancer, Oncol. Ther., 5:17-29 (2017).

Nilsson, S. and Gustafsson, J. A., Estrogen Receptors: Therapies Targeted to Receptor Subtypes, Nature, 89(1):44-55 (2011).

Parisian, A. D. et al., Abstract #1618, Poster #P5-08-07, The Complete Estrogen Receptor Antagonist OP-1250 Can Combine with HER2 Inhibition to Inhibit Estrogen Receptor-driven Cellular Proliferation and Shrink Xenograft Tumors in ER+/HER2+ Breast Cancer Models, presented at the San Antonio Breast Cancer Symposium, Dec. 7-10, 2021.

Parisian, A. D. et al., Abstract P5-08-07: The complete estrogen receptor antagonist OP-1250 can combine with HER2 inhibition to inhibit estrogen receptor-driven cellular proliferation and shrink xenograft tumors in ER+/HER2+ breast cancer models, Cancer Res., 82 (Supp 4):1-4 (2022).

Parisian, A. D. et al., Precision Run-on Sequencing (PRO-Seq) Analysis of a Treatment Time Course in ER+ Breast Cancer Cell Lines Profiles the Transcriptional Changes Underlying Response to Complete Estrogen Receptor Antagonist (CERAN) OP-1250, #5375, presented at the American Associated for Cancer Research, Apr. 8-13, 2022, New Orleans, LA.

Patel, H. et al., Abstract P6-20-08: Anti-tumor activity of elacestrant (RAD1901) in models harboring ESR1 mutations resistant to standard of care therapies, Cancer Res., 79 (Supp 4):1-4 (2019).

Patel, H. K. and Bihani, T., Selective estrogen receptor modulators (SERMs) and selective estrogen receptor degraders (SERDs) in cancer treatment, Pharmacology & Therapeutics, 186:1-24 (2018).

Patel, M. et al., Abstract P1-17-12: Preliminary data from a phase I/II, multicenter, dose escalation study of OP-1250, an oral CERAN/SERD, in subjects with advanced and/or metastatic estrogen receptor (ER)-positive, HER2-negative breast cancer, Cancer Res., 82 (Supp 4):1-4 (2022).

Patel, M. et al., Preliminary Data From a Phase 1/2, Multicenter, Dose Escalation Study of OP-1250, an Oral CERAN/SERD, in Patients With Advanced and/or Metastatic Estrogen Receptor (ER)-Positive, HER2-Negative Breast Cancer, presented at the San Antonio Breast Cancer Symposium, San Antonio, TX, Dec. 7-10, 2021.

Pawlak, K. J. and Wiebe, J. P., Regulation of estrogen receptor (ER) levels in MCF-7 cells by progesterone metabolites, Journal of Steroid Biochem and Mol Biol, 107:172-179 (2007).

Pearce, S. and Jordan, V., The biological role of estrogen receptors a and b in cancer, Critical Reviews in Oncology, 50:3-22 (2004).

Robertson, J. F. et al., Activity of fulvestrant 500 mg versus anastrozole 1 mg as first-line treatment for advanced breast cancer: results from the FIRST study, J. Clin. Oncol., 27(27):4530-5 (2009).

Robertson, J. F. R. et al., Fulvestrant 500 mg versus anastrozole 1 mg for hormone receptor-positive advanced breast cancer (FALCON): an international, randomised, double-blind, phase 3 trial, The Lancet, 388:2997-3005 (2016).

Rugo, H. S. et al., Endocrine Therapy for Hormone Receptor-Positive Metastatic Breast Cancer: American Society of Clinical Oncology Guideline, Journal of Clinical Oncology, 34:1-37 (2016).

Senkus, E. et al., Primary breast cancer: ESMO Clinical Practice Guidelines for diagnosis, treatment and follow-up, Annals of Oncology, 26(Supp5):8-30 (2015).

Sharma, A.P. et al., Structure-activity relationship of antiestrogens. Effect of the side chain and its position on the activity of 2,3-diaryl-2H-1-benzopyrans, J. Med. Chem., 33(12):3216-22 (1990).

Sharma, A.P. et al, Structure-activity relationship of antiestrogens. Phenolic analogues of 2,3-diaryl-2H-1-benzopyrans, J. Med. Chem., 33(12):3222-9 (1990).

(56) References Cited

OTHER PUBLICATIONS

Spoerke, J. M. et al., Heterogeneity and clinical significance of ESR1 mutations in ER-positive metastatic breast cancer patients receiving fulvestrant, Nature Communications, 7:11579 (2016).
Terry, M., Genentech Quietly Shelves Phase II Cancer Contender, BioSpace, published Apr. 28, 2017 (3 pages).
Toy, W. et al., ESR1 ligand binding domain mutations in hormone-resistant breast cancer, Nat Genet., 45(12):1439-1445 (2013).
Ullrich, J. W. and Miller, C. P., Estrogen receptor modulator review, Expert Opinion on Therapeutics Patents, 16(5): 559-572 (2006).
Veeraraghavan, J. et al., Recurrent ESR1-CCDC170 rearrangements in an aggressive subset of oestrogen receptor-positive breast cancers, Nature Communications, 5:4577 (2014).
Verraraghavan, J. et al., Recurrent and pathological gene fusions in breast cancer: current advances in genomic discovery and clinical implications, Breast Cancer Res Treat., 158:219-232 (2016).
Vries, E. et al., Abstract P1-10-04: Elacestrant, a novel oral selective estrogen receptor degrader (SERD), decreases tumoral 18F-FES uptake in a phase 1 study of Er+, HER2 –, advanced breast cancer patients, Cancer Res., 78(Supp 4):1-4 (2018).
Wakeling, A.E. et al, A Potent Specific Pure Antiestrogen with Clinical Potential, Cancer Research, 51(15):3867-3873 (1991).
Wilson, T. M. et al, 3-[4-(1,2-Diphenylbut-1-enyl)phenyl]acrylic acid: a non-steroidal estrogen with functional selectivity for bone over uterus in rats, J. Med. Chem., 37(11): 1550-2 (1994).
Wu, Y.L. et al, Structural basis for an unexpected mode of SERM-mediated ER antagonism, Mol. Cell., 18(14): 413-24 (2005).
Clinical Trials, Phase 1b Study in Combination With a CDK4/6 Inhibitor or With a PI3K Inhibitor, History of Changes for Study: NCT05508906, 8 pages (2023).
International Search Report for PCT/US2021/021151, 6 pages (mailed Jul. 20, 2021).
Roy, D. et al., To Pass or Not To Pass: Predicting the Blood-Brain Barrier Permeability with the 3D-RISM-KH Molecular Solvation Theory, ACS Omega, 4:16774-16780 (2019).
Sledge, G. et al., MONARCH 2: Abemaciclib in Combination With Fulvestrant in Women With HR+/HER2? Advanced Breast Cancer Who Had Progressed While Receiving Endocrine TherapyJournal of Clinical Oncology, 35(25): 2875-2884 (2017).
Weir et al., 'AZD9496: An Oral Estrogen Receptor Inhibitor That Blocks the Growth of ER-Postive and ESR1-Mutant Breast Tumors in Preclinical Models', Cancer Research, 76(11):3307-3318 (2016).
Dustin, D. et al., ESR1 Mutations in Breast Cancer, Cancer, 125(21):3714-3728 (2019).
Kemp, A., Camizestrant demonstrated highly statistically significant and clinically meaningful improvement in progression-free survival in 1st-line advanced HR-positive breast cancer with an emergent ESR1 tumour mutation in SERENA-6 Phase III trial, 3 pages, AstraZeneca PLC (2025).

\* cited by examiner

A.

B.

REGIMENS OF ESTROGEN RECEPTOR ANTAGONISTS

CROSS-REFERENCE TO RELATED APPLICATIONS

The present application is a U.S. National Stage Application of PCT/US20/40863, filed Jul. 6, 2020, which claims priority to U.S. Provisional Application Nos. 62/871,191, filed Jul. 7, 2019, and 62/871,592, filed Jul. 8, 2019, the entirety of each of which is hereby incorporated by reference.

BACKGROUND

The estrogen receptor (ER) plays important roles in various cancers, including breast cancers. A variety of treatments have been developed to target the estrogen receptor and/or its activities.

SUMMARY

There remains a need for anti-estrogen agents that can completely inhibit estrogen receptors, including those coded for by both wild-type and mutant versions (e.g., those containing activating mutations) of the gene encoding Estrogen Receptor-alpha (ERα), Estrogen Receptor 1 (ESR1). Selective estrogen receptor modulators (SERMs) or degraders (SERDs) are a particularly useful or promising tools for such therapy. The estrogen receptor is a tripartite protein comprising two distinct transcriptional activation functions (AF1 and AF2). Complete anti-estrogen activity requires inactivation of both AF1 and AF2. Activating mutations in the gene that codes for estrogen receptor 1 allows for activation of both AF1 and AF2 even in the absence of estrogen.

Previous therapies, such as tamoxifen, AZD9496, and ARN-810 fail to disable both activation functions (i.e., do not disable both AF1 and AF2). As such, there remains a need for therapies that disable both AF1 and AF2 in order to completely inhibit the estrogen receptor, and moreover, there remains a need for therapies that inhibit the estrogen receptor despite activating mutations. The present disclosure documents, among other things, that certain compounds, alone or in combination with other agents, can be used as a treatment for patients or subjects suffering from a cancer, and wherein the patient or subject carries a mutation of estrogen receptor 1 (ESR1). For example, in some embodiments, a compound useful for treatment of patients or subjects suffering from a cancer, and wherein the patient or subject carries a mutation of estrogen receptor 1 (ESR1), is Compound 1:

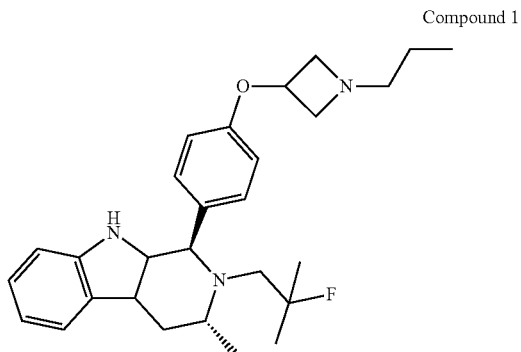

Compound 1

In some embodiments, the present disclosure provides a method of treating a patient or subject suffering from a cancer associated with the estrogen receptor (ER) comprising administration of an estrogen receptor antagonist and a CDK4/6 inhibitor.

In some embodiments, the present disclosure provides a method of treating a patient or subject suffering from a cancer associated with the estrogen receptor (ER) comprising administration of an estrogen receptor antagonist and a PIK3CA inhibitor.

In some embodiments, the present disclosure provides a method of treating a patient or subject suffering from a cancer associated with the estrogen receptor (ER) comprising administration of an estrogen receptor antagonist and an mTOR inhibitor.

In some embodiments, the present disclosure provides a method of treating a patient or subject suffering from a cancer, wherein the cancer has metastasized to the brain, bones, lungs, or liver, comprising administrating to the patient or subject Compound 1:

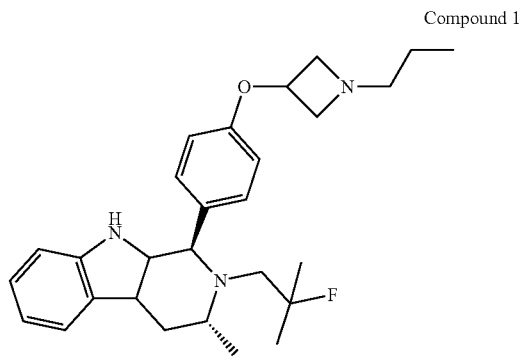

Compound 1

In some embodiments, the present disclosure provides an assay system for assessing compounds or compositions for inhibition of estrogen receptor activating function 1 (AF1) and/or activating function 2 (AF2).

In some embodiments, the present disclosure provides a method for treating a patient suffering from a cancer, the method comprising oral administration of Compound 1.

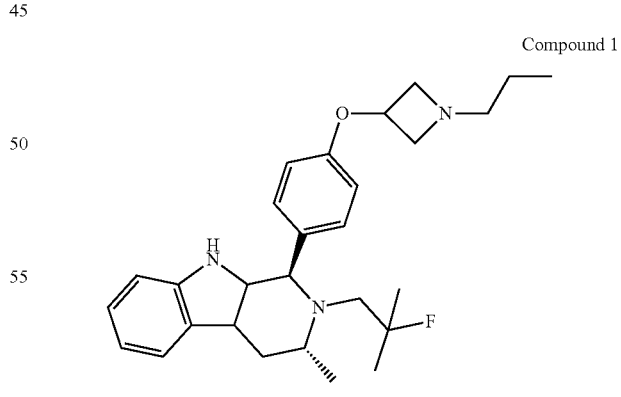

Compound 1

DETAILED DESCRIPTION OF CERTAIN EMBODIMENTS

Figure 1A:
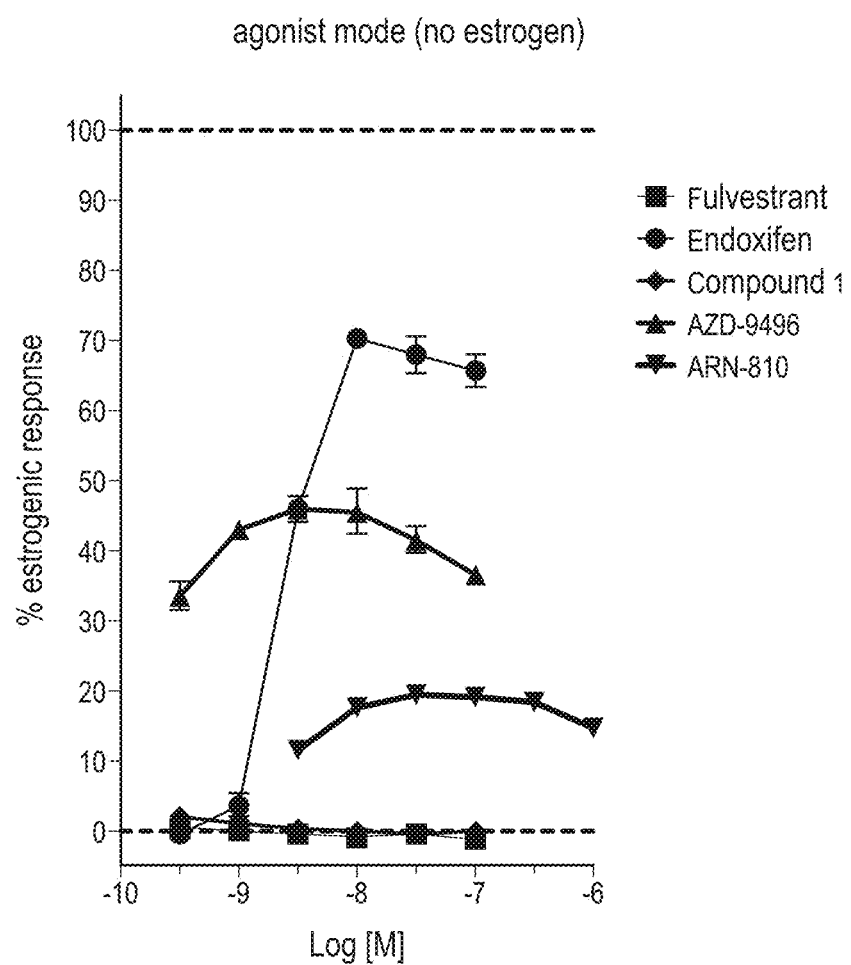
FIG. 1A is a scatter plot measuring percent of estrogenic response as a function of Log [M] for certain estrogen receptor antagonist compounds where no estrogen has been added.

There remains a need for therapies of estrogen receptor (ER) positive cancer types that overcome the problems associated with previous methods. The present disclosure provides, among other things, methods of treating patients or subjects suffering from a cancer related to the estrogen receptor, and mutations of the estrogen receptor, comprising administering an estrogen receptor antagonist. In some embodiments, the estrogen receptor antagonist is Compound 1:

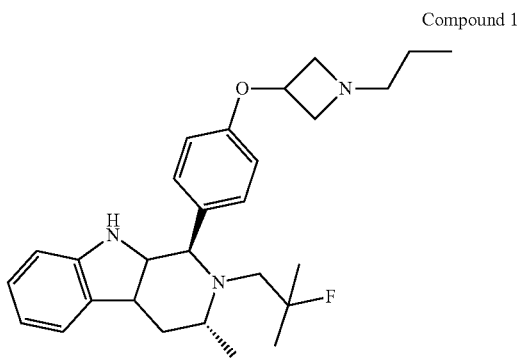 [SMILES: CCCN1CC(Oc2ccc([C@@H]3C4Nc5ccccc5C4C[C@@H](C)N3CC(C)(C)F)cc2)C1]

Compound 1 or a pharmaceutically acceptable salt thereof.

Definitions

Administration: As used herein, the term "administration" typically refers to the administration of a composition to a subject or system, for example to achieve delivery of an agent that is, or is included in or otherwise delivered by, the composition.

Agent: As used herein, the term "agent" refers to an entity (e.g., for example, a lipid, metal, nucleic acid, polypeptide, polysaccharide, small molecule, etc., or complex, combination, mixture or system [e.g., cell, tissue, organism] thereof), or phenomenon (e.g., heat, electric current or field, magnetic force or field, etc.).

Antagonist: As used herein, the term "antagonist" may refer to an agent, or condition whose presence, level, degree, type, or form is associated with a decreased level or activity of a target. An antagonist may include an agent of any chemical class including, for example, small molecules, polypeptides, nucleic acids, carbohydrates, lipids, metals, and/or any other entity that shows the relevant inhibitory activity. In some embodiments, an antagonist may be a "direct antagonist" in that it binds directly to its target; in some embodiments, an antagonist may be an "indirect antagonist" in that it exerts its influence by means other than binding directly to its target; e.g., by interacting with a regulator of the target, so that the level or activity of the target is altered). In some embodiments, an "antagonist" may be referred to as an "inhibitor".

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: As used herein, the term "excipient" refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Patient or subject: As used herein, the term "patient" or "subject" refers to any organism to which a provided composition is or may be administered, e.g., for experimental, diagnostic, prophylactic, cosmetic, and/or therapeutic purposes. Typical patients or subjects include animals (e.g., mammals such as mice, rats, rabbits, non-human primates, and/or humans). In some embodiments, a patient is a human. In some embodiments, a patient or a subject is suffering from or susceptible to one or more disorders or conditions. In some embodiments, a patient or subject displays one or more symptoms of a disorder or condition. In some embodiments, a patient or subject has been diagnosed with one or more disorders or conditions. In some embodiments, a patient or a subject is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amounts appropriate for administration in a therapeutic regimen to a relevant subject (e.g., in amounts that have been demonstrated to show a statistically significant probability of achieving a predetermined therapeutic effect when administered), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66:1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition.

Therapeutically effective amount: As used herein, the term "therapeutically effective amount" refers to an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder and/or condition. In some embodiments, a therapeutically effective amount is administered in a single dose; in some embodiments, multiple unit doses are required to deliver a therapeutically effective amount.

The Estrogen Receptor

The estrogen receptor ("ER") is involved in a variety of biological processes, relating, for example, to development of the female reproductive system, maintenance of bone mass, protection of cardiovascular and/or central nervous system components, etc (see, for example, Pearce & Jordan *Crit. Rev. Onc/Hem* 50:3, 2004; Heldring *Phys. Rev.* 87:905, 2007).

Figure 11:
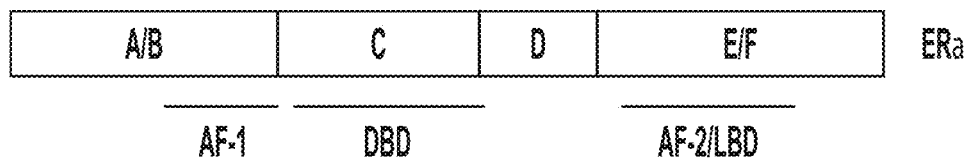
FIG. 11 is a reproduction of FIG. 1A of Patel & Bihani *Pharm & Therap* 186:1, 2018, illustrating that mammals express two major isoforms of the ER, known as ERα and ERβ, each of which is a member of the nuclear hormone receptor family. A) The A-F domains that constitute the estrogen receptor, which include the activation function 1 (AF1) domain, the DNA binding domain (DBD), the hinge region, and the ligand binding domain (LBD)/activation function 2 (AF2 domain). B) The effects of endocrine therapies (aromatase inhibitors, SERMs, and SERDs) on the estrogen receptor pathway. Aromatase inhibitors prevent ER signaling by inhibiting synthesis of estradiol, SERMs prevent ER signaling by binding to ER and causing an inactive complex, and SERDs prevent ER signaling by causing degradation of ER.
Figure 11:
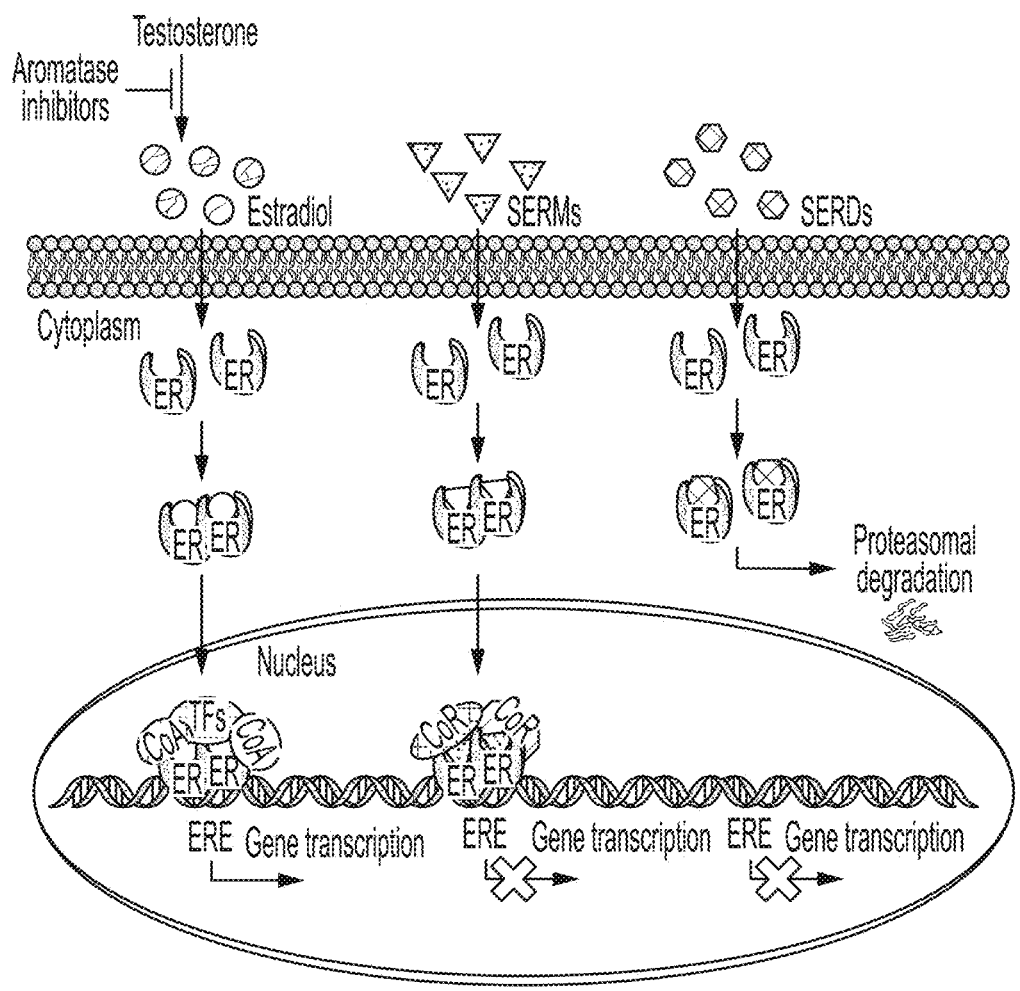

Mammals express two major isoforms of the ER, known as ERα and ERβ, each of which is a member of the nuclear hormone receptor family and has a structural organization as depicted in FIG. 1A of Patel & Bihani Pharm & Therap 186:1, 2018, reproduced in FIG. 11. As illustrated in FIG. 11: A) The A-F domains that constitute the estrogen receptor, which include the activation function 1 (AF1) domain, the DNA binding domain (DBD), the hinge region, and the ligand binding domain (LBD)/activation function 2 (AF2 domain). B) The effects of endocrine therapies (aromatase inhibitors, SERMs, and SERDs) on the estrogen receptor pathway. Aromatase inhibitors prevent ER signaling by inhibiting synthesis of estradiol, SERMs prevent ER signaling by binding to ER and causing an inactive complex, and SERDs prevent ER signaling by causing degradation of ER.

As can be seen, six ER "domains", labeled A-F, have been defined in the ER structure. Domain A/B, found at the amino-terminal end of the ER protein, is the largest domain and includes one of the two so-called "transcriptional activation function" elements, AF1; AF2 is found in the E domain, which also includes the ligand-binding domain and element(s) that are believed to participate in ER dimerization and nuclear localization (see, for example, Hewitt & Korach Endocrine Rev 39:664, 2018). It is believed that binding of ligand to the ligand-binding domain triggers a structural re-organization of alpha-helices within the E domain, and this reorganization may contribute to activity of AF2 (e.g., in interacting with certain mediator components).

The ER's C domain includes its DNA binding domain, which mediates interaction with so-called "estrogen responsive element(s)" (ERE(s)) operatively associated with genes whose transcription is regulated by the ER. ERα and ERβ regulate expression of different ERE-associated genes, and show different cellular and tissue distribution patterns. DNA binding by the ER appears to be mediated by two zinc finger structures within the C domain, although additional element(s) may contribute (see, for example, Hewitt & Korach *Endocrine Rev* 39:664, 2018). The ER's C domain may also participate in or otherwise contribute to ER dimerization.

The ER's D domain is also called the "hinge region" and includes amino acid element(s) that may participate in ER dimerization and/or nuclear localization.

The ER's F domain may play a role in ER protein stability. This domain appears to be characteristic of estrogen receptors, as compared with other nuclear receptor family members, and may contribute to responsiveness to certain therapies (e.g., tamoxifen) (see, for example, Arao et al, *J. Bio. Chem* 293:22, 8495).

Figure 3A:
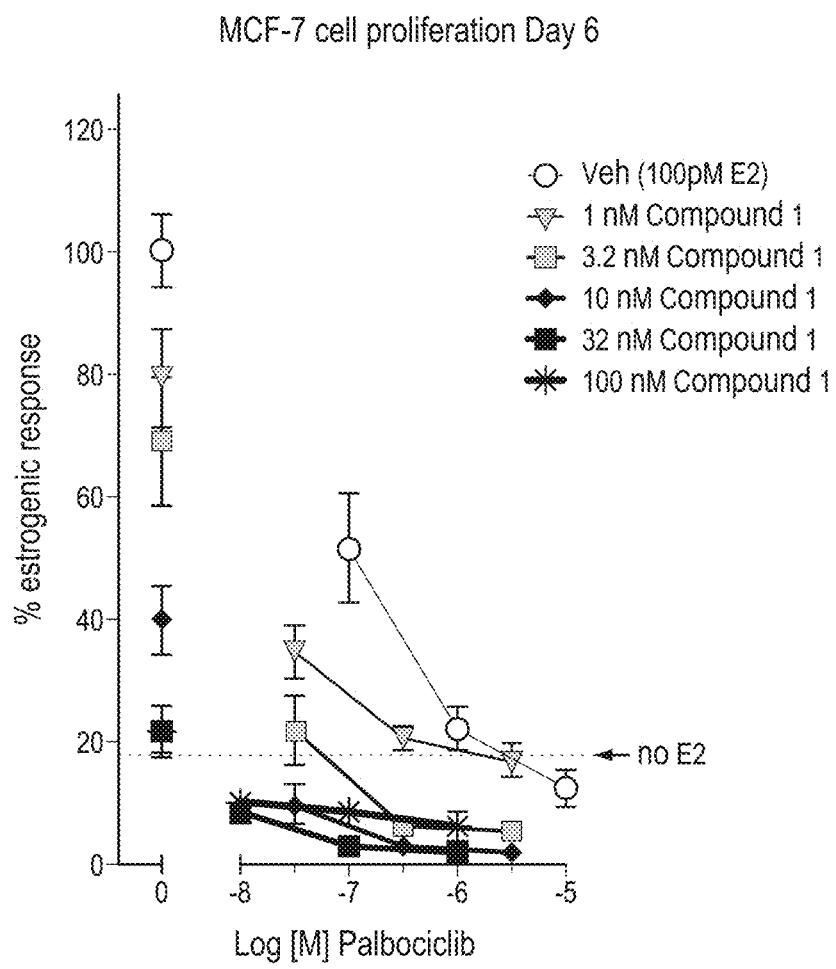
FIGS. 3A-3C are scatter plots illustrating the decreased percent of estrogen response for Compound 1 in combination with various CDK4/6 inhibitors.
Figure 3B:
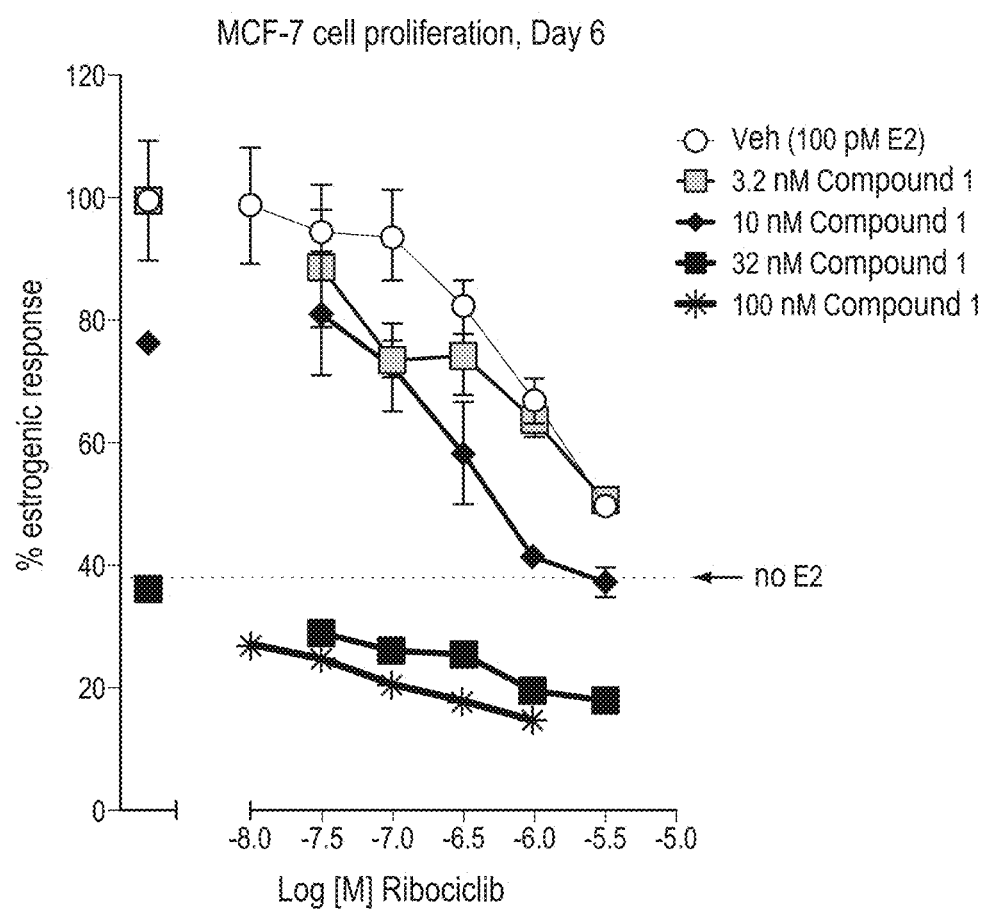
Figure 3C:
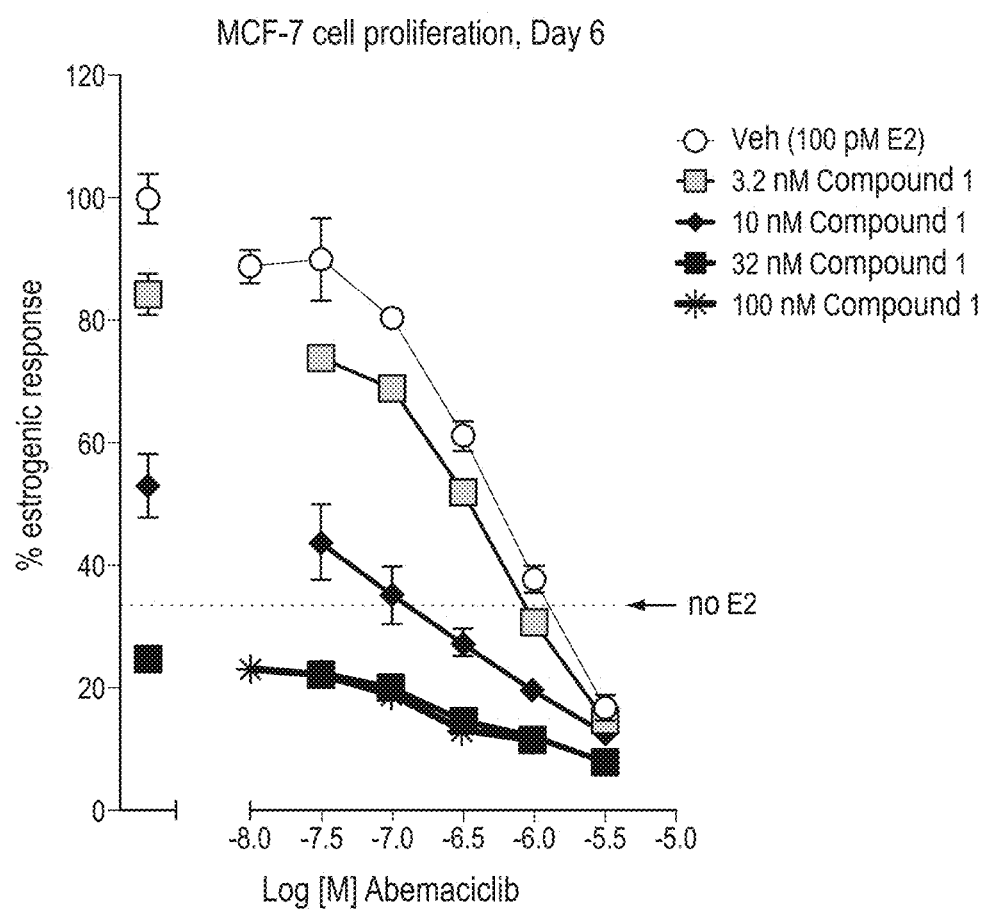

In the presence of a natural ligand (e.g., 17β-estradiol), the ER undergoes a conformational change, homodimerizes, and localizes to the nucleus, where it binds to EREs and regulates transcription of its target genes (see, for example, Pawlak et al.; Kumar & Chambor; Hall & McDonnell); this series of events has been described as the "genomic" mechanism of ER gene regulation. Other mechanisms, such as "tethered", "non-genomic", and "ligand-independent", have also been described, as depicted in FIG. 3 of Hewitt & Korach, reproduced in FIG. 12.

Figure 12:
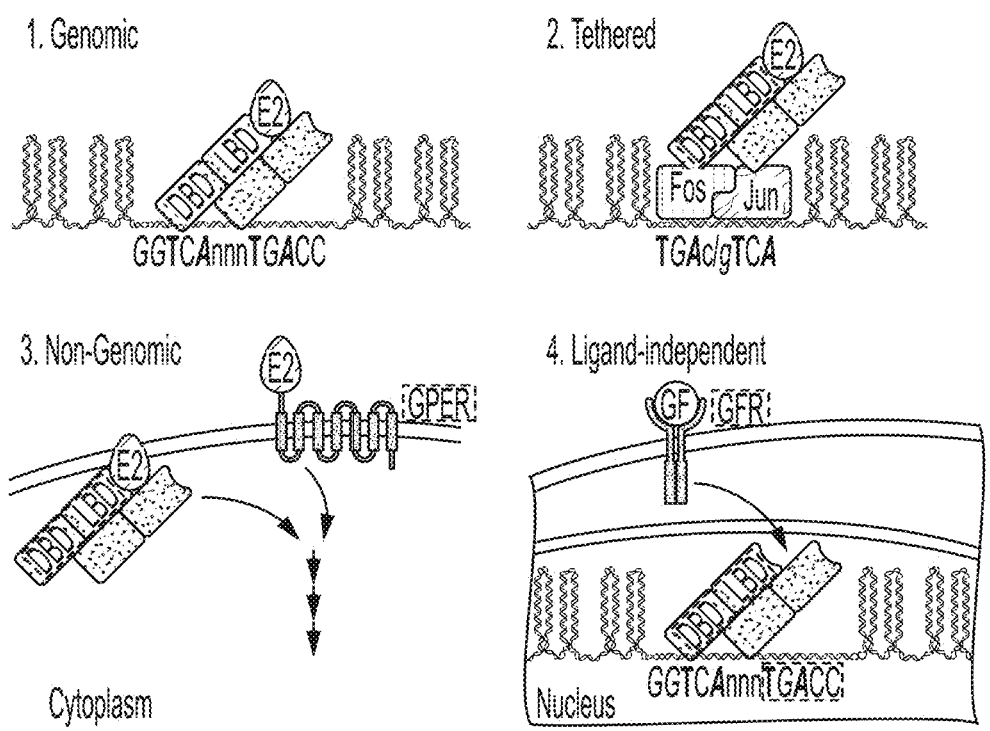
FIG. 12 is a reproduction of FIG. 3 of Hewitt & Korach *Endocrine Rev.* 39:664-674 (Jun. 12, 2018), illustrating variations in the basic mechanism of E2 response.

As illustrated in FIG. 12 and reported by Hewitt & Korach, variations in the basic mechanism of E2 response. Four different E2 response mechanisms have been described. (1) The genomic mechanism involves interaction between ER and ERE DNA motifs. (2) The tethered mechanism involves indirect interaction between ER and other transcriptional regulators, such as the AP1 DNA motif that binds the FOS/JUN dimer. Thus, ER is "tethered" to the DNA via, in this example, FOS/JUN binding to its AP1 DNA motif. (3) Nongenomic signaling is so-called because it initiates a signal from extracellular E2 that leads to rapid signal cascades in the cytoplasm, and thus the response does not involve interaction with genomic features. The responses are mediated by membrane-associated ER, or by GPER, a G protein-coupled receptor. (4) Ligand-independent signaling involves transduction of extracellular growth factor (GF) activation of cell membrane GF receptor (GFR), which initiates signaling cascades, such as MAPK. The signal is received by the ER, activating its transcriptional modulation of target genes, despite lacking E2 ligand.

The ER has been implicated in a variety of cancers. In many tumors that express the estrogen receptor (i.e., ER$^+$ tumors), active ERα signaling has been demonstrated to drive cell proliferation (although ERβ signaling has been reported to be able to achieve tumor suppressor effects; see, for example, Nilsson & Gustafson *Clin. Pharmacol. Ther.* 89:44, 2011). Typically, tumors (e.g., breast tumors) with as few as 1% of cells staining positive for ER are classified as "ER$^+$".

Therapies targeting the ER are standard of care for many patients with ER$^+$ tumors (see, for example, Cardoso et al *Annals Onc.* https://doi.org/10.1093/announc/mdmx036, 2017; Rugo et al. *J. Clin. Oncol.* 34:3069, 2016; Senkus et al *Annal Onc.* 26: v8, 2015; Sareddy & Vadlamudi *Clin. J Nat. Med,* 13:801, 2015). For early stage breast cancer patients, for example, recommended therapy typically involves tumor resection, followed by ER-targeted therapy (e.g., as discussed below). For advanced breast cancer, including metastatic breast cancer, ER-targeted therapy is the mainstay.

Estrogen-Receptor-Targeted Therapies

Given the importance of ER signaling in many cancers, as well as in certain cardiovascular, inflammatory, and neurodegenerative diseases, significant effort has been invested in developing therapeutic agents and modalities that target the ER. There is some fluidity/flexibility in terminology that has been used to describe ER-targeting agents, but a variety of agents, with different mechanisms, have been developed and/or studied.

Some ER-targeting agents are designed and/or documented to reduce levels of estrogen (i.e., 17β estradiol) production.

Some ER-targeting agents are designed and/or documented to bind directly to the ER; in some cases, such agents compete with estrogen for binding to the ER and/or interfere with the allosteric changes that estrogen binding would naturally produce. Often, the term "antiestrogen" is used to refer to agents that bind to the ER, and sometimes is specifically used to indicate those agents that compete with estrogen for ER binding.

The term "selective estrogen receptor modulator," ("SERM"), has been used to refer to compounds that are designed and/or documented to alter some aspect of ER activity. Some writings refer to "SERMs" as representing a particular type of anti-estrogens; other writings, however, use the term "SERM" more generally, to refer to a compound that specifically impacts some feature of ER (particularly ERα) expression and/or activity.

The term "selective estrogen receptor degrader" ("SERD") has been used to refer to compounds that are designed and/or documented to trigger or enhance degradation of the ER. In many instances, if presence of a compound correlates with reduced level of ER, the compound may be referred to as a SERD. Some writings classify compounds either as SERMs or as SERDs; others refer to SERDs as a particular type, or species, of compounds that are SERMs.

Regardless of mechanism of action of a particular agent, clinical experience thus far has revealed that incomplete effects (e.g., within an individual patient and/or across patient populations) and/or development of resistance remain a problem.

Among other things, presence or development of certain ER mutations has been reported to impact effectiveness of various ER-targeted therapies (see, for example, Jeselsohn et al *Nature Rev. Clin. Onc.* 12, 573, 2015; Gelsomino et al. *Breast Cancer Res. Treat* 157:253, 2016; Toy et al. 2013). Some particularly problematic mutations are those that "activate" one or more aspects of ER expression and/or function; some activating mutations have been reported that can render the ER ligand-independent (i.e., constitutively active). For example, particular mutations in the ER ligand binding domain, including D538G and Y537S, have been demonstrated to constitutively activate the ER; other mutations including deletions and/or fusions that remove the ligand binding domain, can have similar effects (see, for example, Li et al. *Cell Repts* 4:1116, 2013; Veeraraghavan et al *Breast Cancer Research and Treatment* 158, 219-232, 2016; Veeraraghavan, et al. *Nature Comms* 5:4577, 2014). Some reports have indicated that as many as 50% of women with metastatic breast cancer may have activating ER mutations detectible in circulating tumor DNA.

Estrogen Receptor Antagonists

As discussed above, enormous investment has been, and continues to be, made in the pursuit of effective therapies that target the ER (reviewed, for example, in Patel & Bihani *Pharmacol. & Therap.* 186:1, 2018).

Among the most advanced compounds under clinical development are:
a. Tamoxifen, which has been an important breast cancer therapeutic, credited with having "saved the lives of half a million women around the world" (see "Bringing the Investigational Breast Cancer Drug Endoxifen From Bench to Bedside with NCI Support, available at https://www.cancer.gov/news-events/cancer-currents-blog/2017/endoxifen-breast-cancer-NCI-support (last accessed Jul. 7, 2019), but known to be less effective in women with low CYP2D6 activity, and also susceptible to development of resistance.
b. Endoxifen, the active metabolite of Tamoxifen, originally developed to address Tamoxifen's failure in women with low CYP2D6 activity, which reduces their ability to convert Tamoxifen into Endoxifen. (see *Cancer Currents Blog*, National Cancer Institute, Aug. 31, 2017).
c. ARN-810 (Brilanestrant; GDC-810), which has been described as "a novel, potent, non-steroidal, orally bioavailable, selective ER antagonist/ER degrader that induces tumor regression in tamoxifen-sensitive and resistant ER+ BC xenograft models" (see Dickler et al. *Cancer Res.* 75 (15 Suppl): Abstract nr CT231, 2015), and which was carried into Phase II clinical trials for treatment of patients with ER+ breast cancer who had failed other hormonal agents, but whose further development may subsequently have been dropped (see, for example, *Biospace* Apr. 27, 2017).
d. AZD9496, which has been described as "an oral nonsteroidal, small-molecule inhibitor of estrogen receptor alpha (ERα) and a potent and selective antagonist and degrader of ERα" (see Hamilton et al *Clin Cancer Res* 1:3519, 2018); AZD9496 has been reported to "antagoni[ze] and degrad[e] ER with anti-tumour activity in both endocrine-sensitive and endocrine-resistant models", and has been described as "comparable to fulvestrant in antagonising ER and circumventing endocrine resistance" (see, Nardone et al. *Br. J. Cancer* 120:331, 2019).
e. RAD-1901 (Elacestrant) has been described as "a novel, non-steroidal oral SERD that has demonstrated single-agent activity in heavily pre-treated patients with ER+ advanced breast cancer (see de Vries et al, *Cancer Res*. Abstract P1-10-04, 2018; see also Bardia et al. *J. Clin. Onc.* 35: 15_suppl, 1014, 2017). Preclinical studies have also reported that "Elacestrant significantly inhibited the growth of xenograft models harboring ESR1 mutations, including those harboring Y537S or D538G mutations and models that were insensitive to fulvestrant and tamoxifen" (see Patel et al. *Cancer Res* 79: Abstract nr P6-20-08, 2019).
f. Fulvestrant (Faslodex™) was the first SERD to earn FDA approval, and has been approved for treatment of certain ER+ cancers, including in combination with palbociclib or abemaciclib. Fulvestrant is a "selective estrogen receptor degrader that binds, blocks and degrades the estrogen receptor (ER), leading to complete inhibition of estrogen signaling through the ER" (see Nathan & Schmid *Oncol Ther* 5:17, 2017). Fulvestrant has achieved significant clinical success, and is often considered to be the "gold standard" against which ER-targeted therapies are compared. However, Fulvestrant is administered by injection rather than orally, and in fact requires administration of 500 mg via intramuscular injection once per month (after initial dosing). Also, although certain retrospective analyses have offered hope that Fulvestrant might have some usefulness in treatment of patients with ER mutants, conclusive evidence of activity has not been achieved (see, for example, Fribbens et al. *J Clin Oncol.* 34:2961, 2916; Spoerke et al. *Nat Commun* 7:11579, 2016):

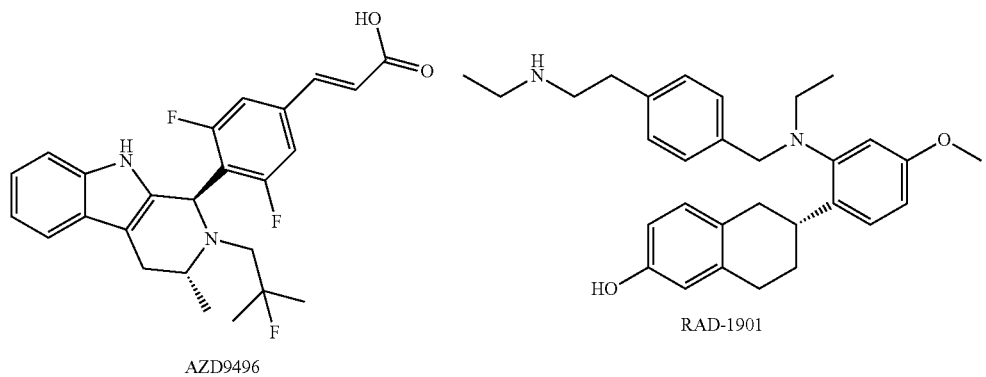

AZD9496

RAD-1901

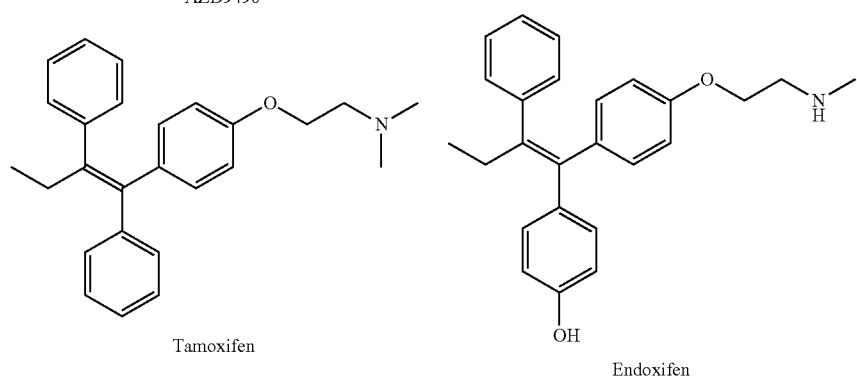

Tamoxifen

Endoxifen

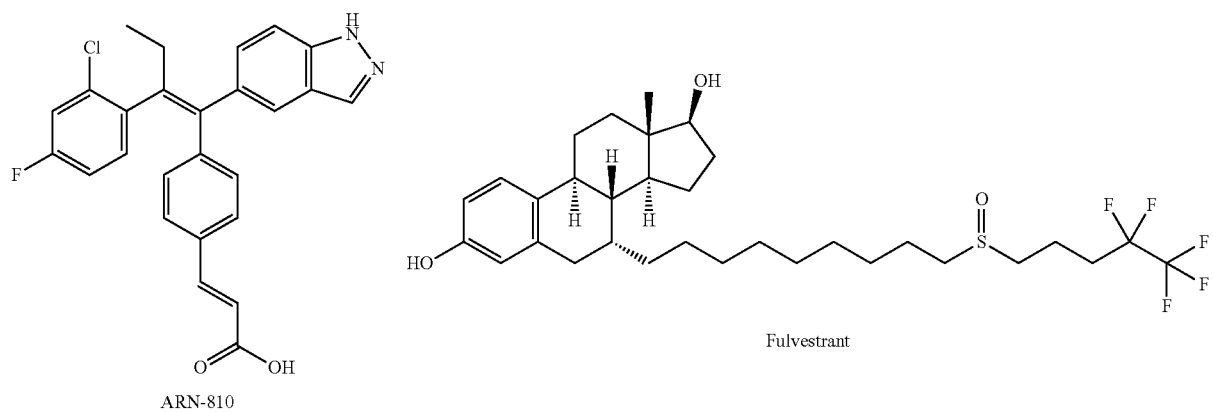

ARN-810

Fulvestrant

The present disclosure appreciates that Fulvestrant's success stems from its ability to function as a complete estrogen receptor antagonist (a "CERAN") that (1) inhibits both AF1 and AF2, so that it can inhibit AF1 activity that remains present in constitutively active ER mutants; (2) promotes ER degradation; and (3) lacks the partial ER agonist activity observed with certain other agents (see, for example, FIG. 1A which, among other things, documents that each of ARN-810, AZD-9496, and Endoxifen increases ER activity in the absence of added estrogen, even while reducing ER activity when estrogen is there). As compared, for example, with therapies that limit estrogen production (e.g., anastrozole) or with partial antagonists (e.g., tamoxifen), fulvestrant exhibits superior activity and is the preferred treatment option for patients with hormone receptor-positive locally advanced or metastatic breast cancer. See Robertson, et al., The Lancet, 388 (10063): 2997-3005 (Dec. 17, 2016). Without wishing to be bound by any particular theory, it is proposed that Fulvestrant's ability to inhibit both AF1 and AF2 may be attributable to its recruitment of co-repressors to the ER complex.

Regardless, the present disclosure further appreciates that many other compounds, including for example, ARN-810, AZD9496, tamoxifen, and others, are less effective than fulvestrant at least in part because they only partially antagonize ER, and specifically because they inhibit activation of AF2 but not AF1.

The present disclosure provides the important and unexpected insight that a previously-described compound, (1R, 3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole ("Compound 1"; see PCT App. Pub. No. WO 2017/059139, the entirety of which is incorporated by reference)

Compound 1

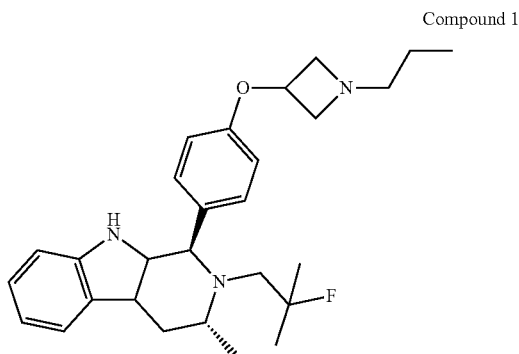 [SMILES: CCCN1CC(Oc2ccc([C@@H]3C4Nc5ccccc5C4C[C@@H](C)N3CC(C)(C)F)cc2)C1]

Compound 1

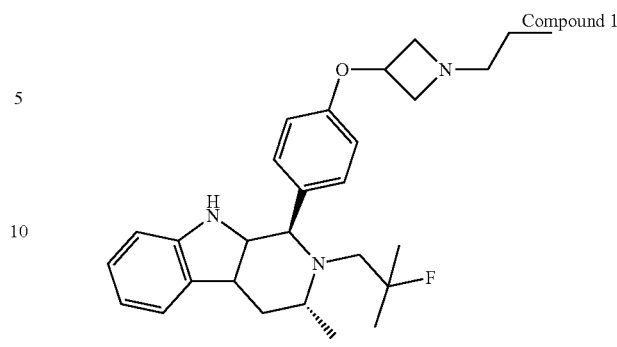

matches Fulvestrant's CERAN attributes, and furthermore offers further valuable properties, including, for example that it (i) is orally bioavailable and has a long half-life; and (ii) shows good blood brain barrier penetration. Among other things, the present disclosure demonstrates that Compound 1 is uniquely useful in certain contexts, including for (a) treatment of cancers associated with ER mutations, including ligand-independent/constitutive mutations; (b) treatment of cancers with CNS (e.g., brain) metastases or tumors; (c) use in combination with certain other agents, including certain agents demonstrated or proposed to be useful with Fulvestrant.

For example, among other things, the present disclosure reports a discovery that Compound 1 exhibits complete estrogen receptor antagonism, and furthermore that such antagonism is comparable to Fulvestrant in various assays. Among other things, as reported in Example 4, the present disclosure demonstrates that Compound 1 is characterized by an ability to inhibit AF1 and AF2, and therefore is properly described as a "complete estrogen receptor antagonist."

The present disclosure teaches that Compound 1 may be particularly useful or effective for treatment of diseases, disorders, or conditions (e.g., cancers) associated with presence of one or more ER mutants, specifically including ligand-independent ER mutants. Thus, in some embodiments, the present disclosure provides methods of treatment in which Compound 1 is administered to a subject who expresses (e.g., in relevant cells or tissues) one or more ERs, and particular one or more ligand-independent ERs; in some embodiments, such subject(s) has been demonstrated to express such mutant ER(s) prior to the administration.

Those skilled in the art will be aware of a variety of technologies that permit detection of a mutant ER in a sample from a subject. In some embodiments, a mutant ER protein is detected; in some embodiments, a nucleic acid encoding a mutant protein (e.g., a mutant ESR1 gene) is detected.

The ability of Compound 1 to inhibit both AF1 and AF2 allows Compound 1 to function as a CERAN despite an activating mutation of the estrogen receptor (e.g., ESR1).

Accordingly, in some embodiments, the present disclosure provides methods of treating a subject (or a population of subjects) suffering from a cancer, wherein the subject is carrying an ESR1 mutation (and/or is expressing a mutant ER protein), the method comprising administering to the subject Compound 1:

or a pharmaceutically acceptable salt thereof.

Assessment of ER Antagonists

Among other things, the present disclosure teaches that useful ER antagonist agents are ones with CERAN activity as described herein.

One aspect of the present disclosure is an insight that conventional strategies for assessing or characterizing ER antagonist (and/or potential antagonist) agents were insufficient at least in that they typically did not distinguish between SERDs and CERANs. In particular, most such conventional strategies did not assess an agent's ability to specifically impact AF1.

Among other things, the present disclosure teaches that particularly useful ER antagonist agents are those that can inhibit ligand-independent ER activity; in some embodiments including activity observed with constitutive ER variant(s) such as, for example, AF2 deletions or truncations and/or LBD mutants (e.g., D538G and Y537S).

Furthermore, the present disclosure teaches that particularly useful ER antagonist agents are characterized by each of:
  a. Inhibition of AF1 (e.g., inhibition of at least one, and preferably all known, constitutive ER variants)
  b. Inhibition of AF2 (e.g., inhibition of ligand-dependent ER activity)
  c. Promotion of ER degradation Additionally, in some embodiments, particularly useful ER antagonist agents are further characterized by one or more of:
  a. Oral bioavailability and a long half-life.
  b. Blood brain barrier penetration.

In particular embodiments, activity of ER antagonist agent(s) may be assessed relative to that of one or more of ARN-810, AZD9496, Endoxifen, Fulvestrant, RAD1901, Tamoxifen, and/or Compound 1; in some such embodiments, comparison is contemporaneous, or alternatively, in some embodiments, it may be with a historical record or future result.

Combination Therapy

Figure 4A:
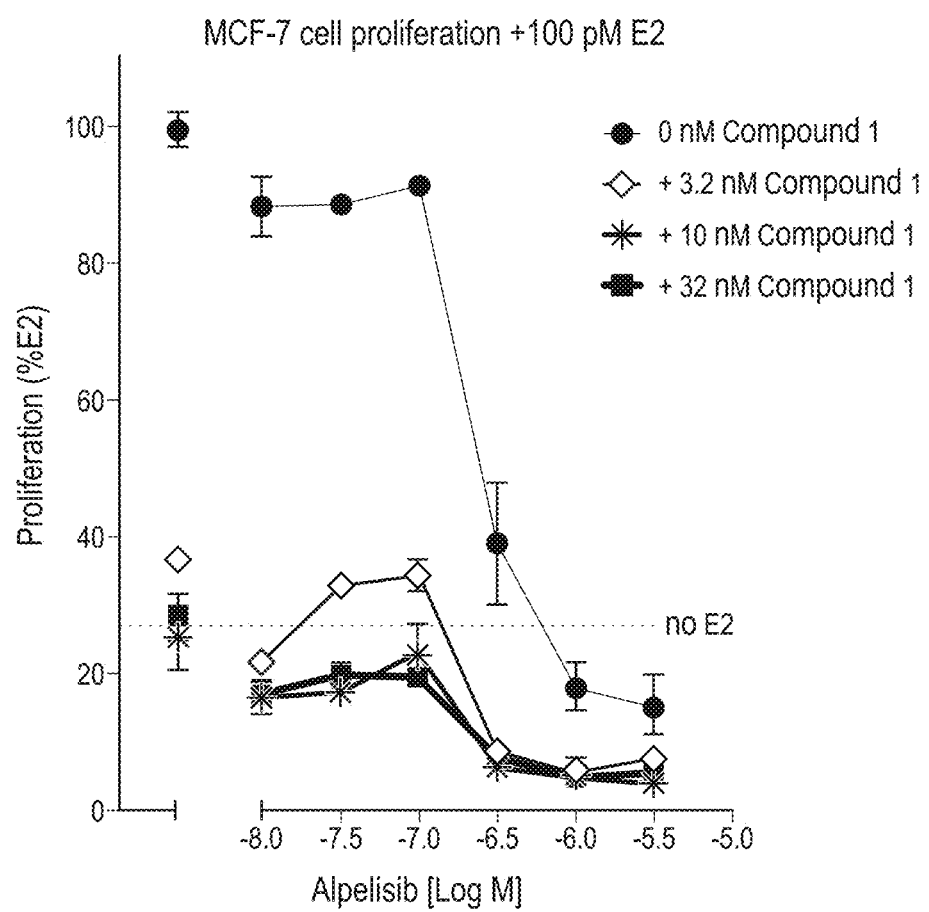
FIGS. 4A-4B are scatter plots illustrating the decreased percent of estrogen proliferation to MCF-7 cells when treated with Compound 1 in combination with a PIK3CA inhibitor.
Figure 4B:
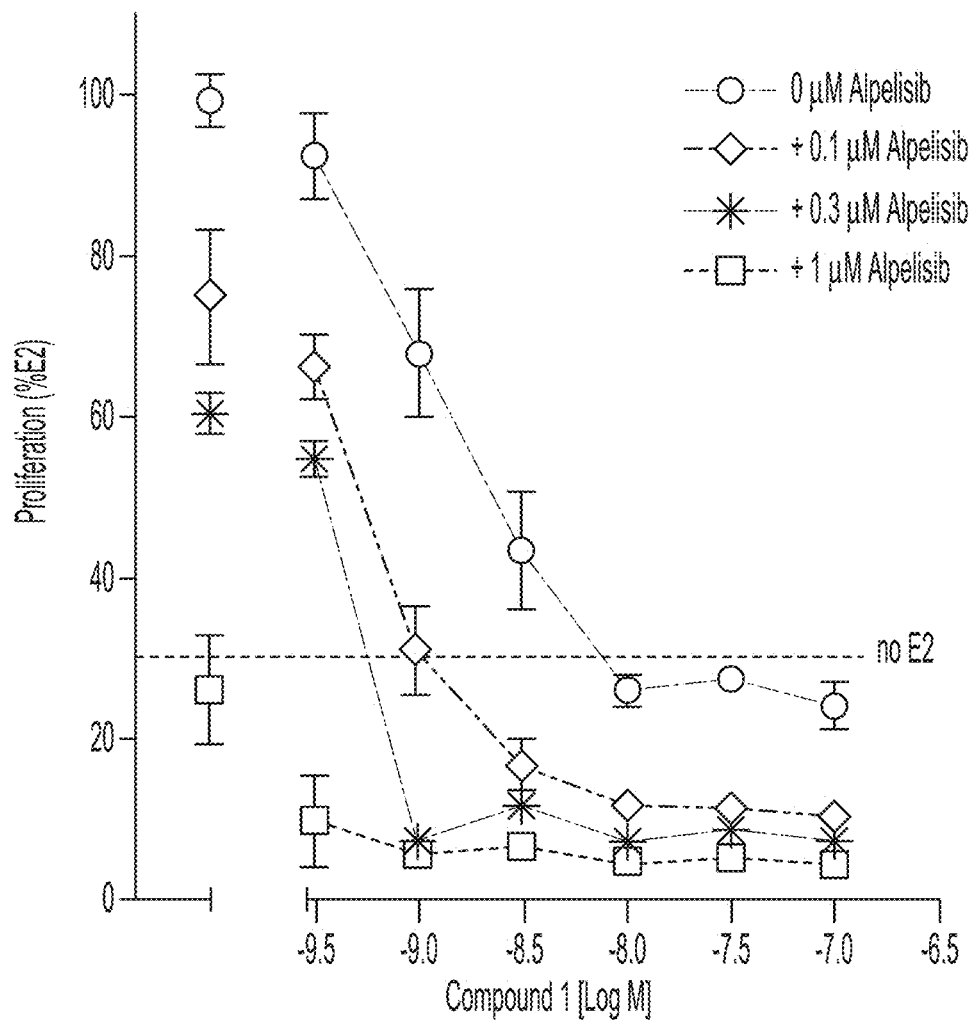
Figure 5A:
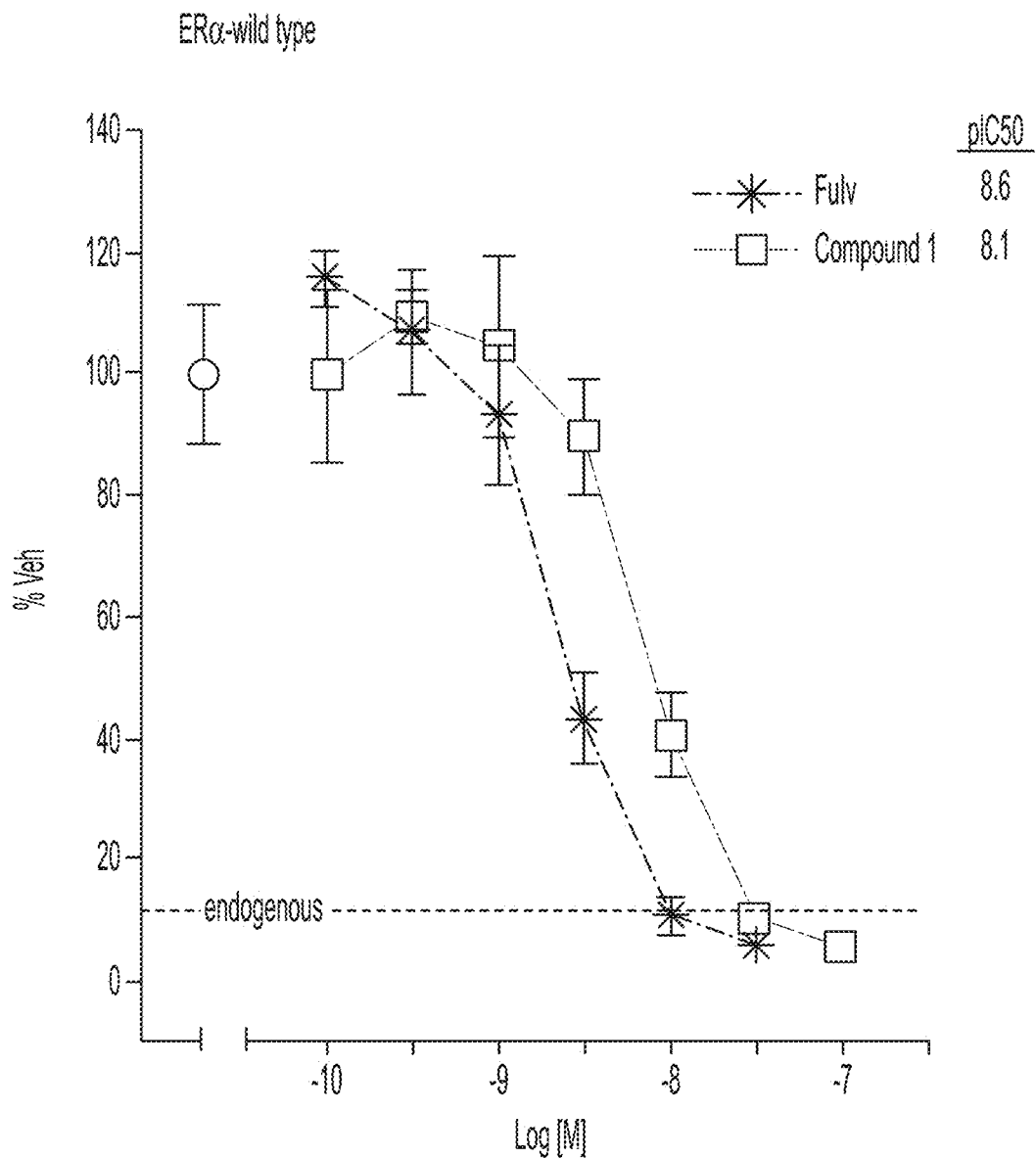
FIGS. 5A-5F are scatter plots for cell lines illustrating dose response of Compound 1 for AF1 inhibition with most common ESR1 mutations.
Figure 5B:
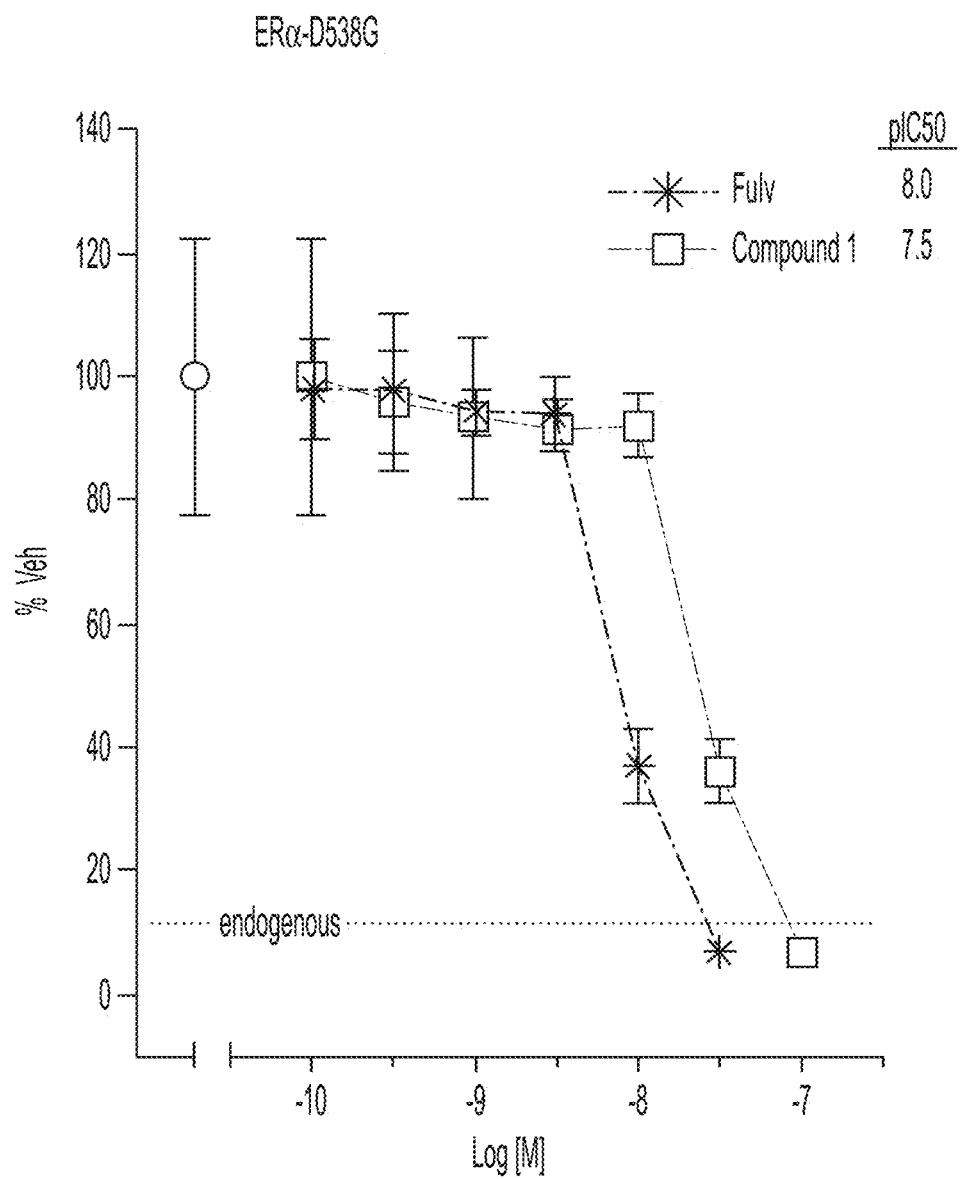
Figure 5C:
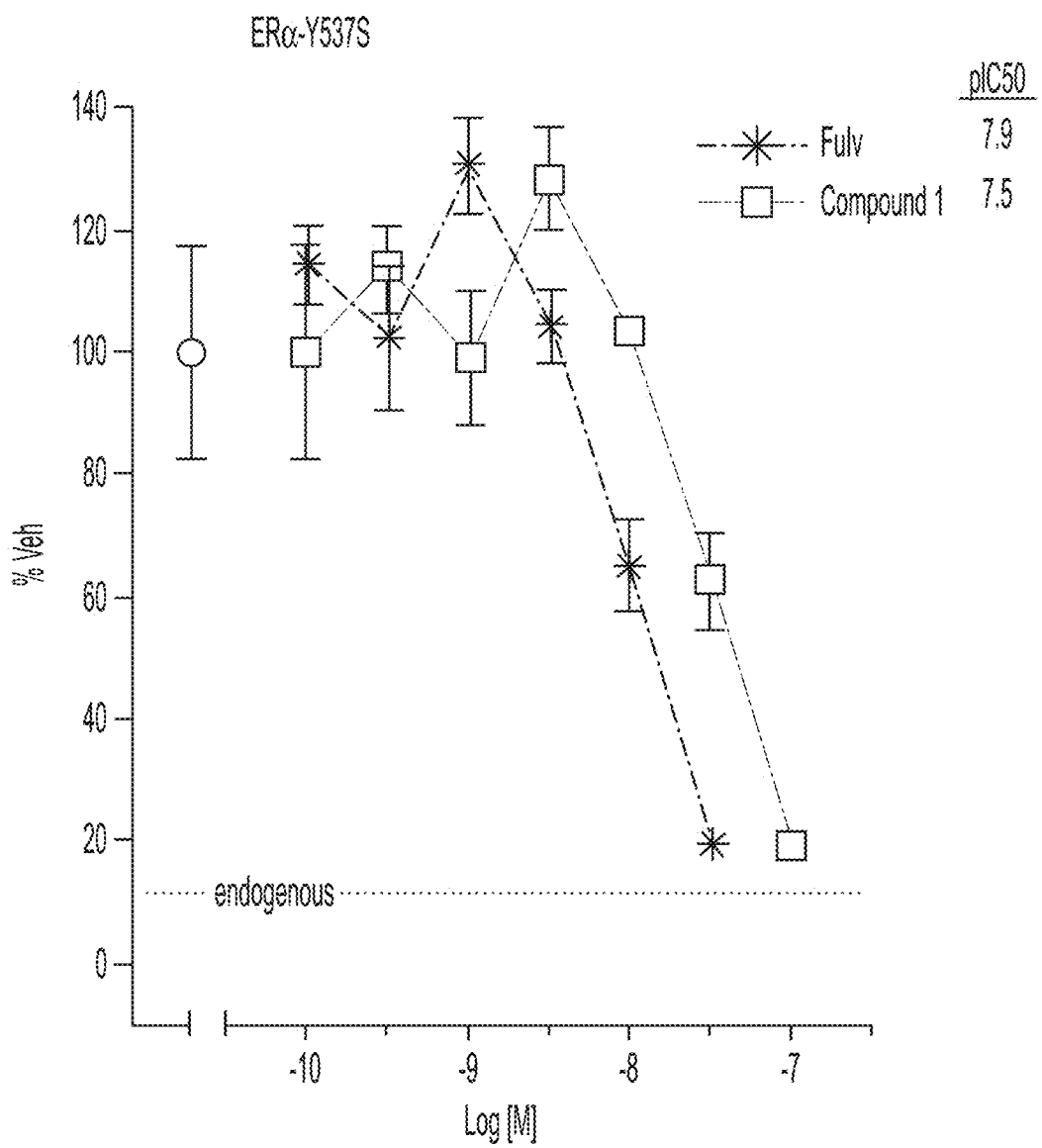
Figure 5D:
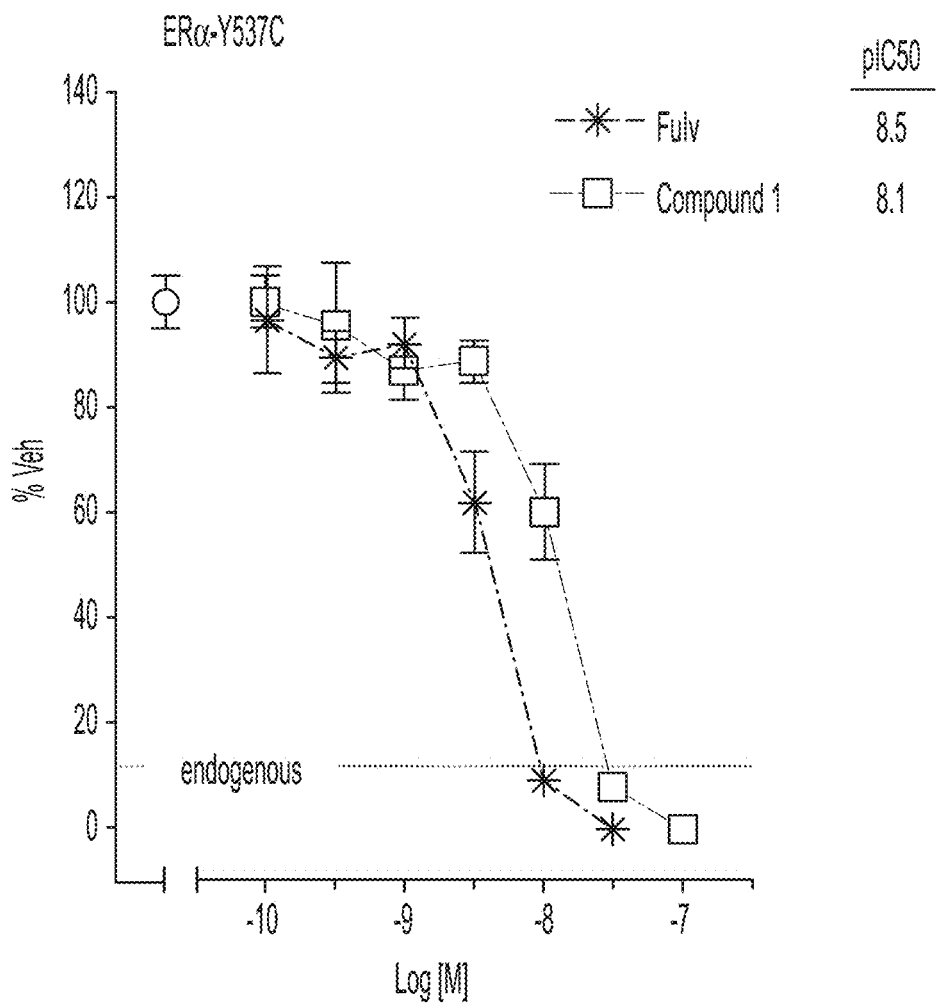
Figure 5E:
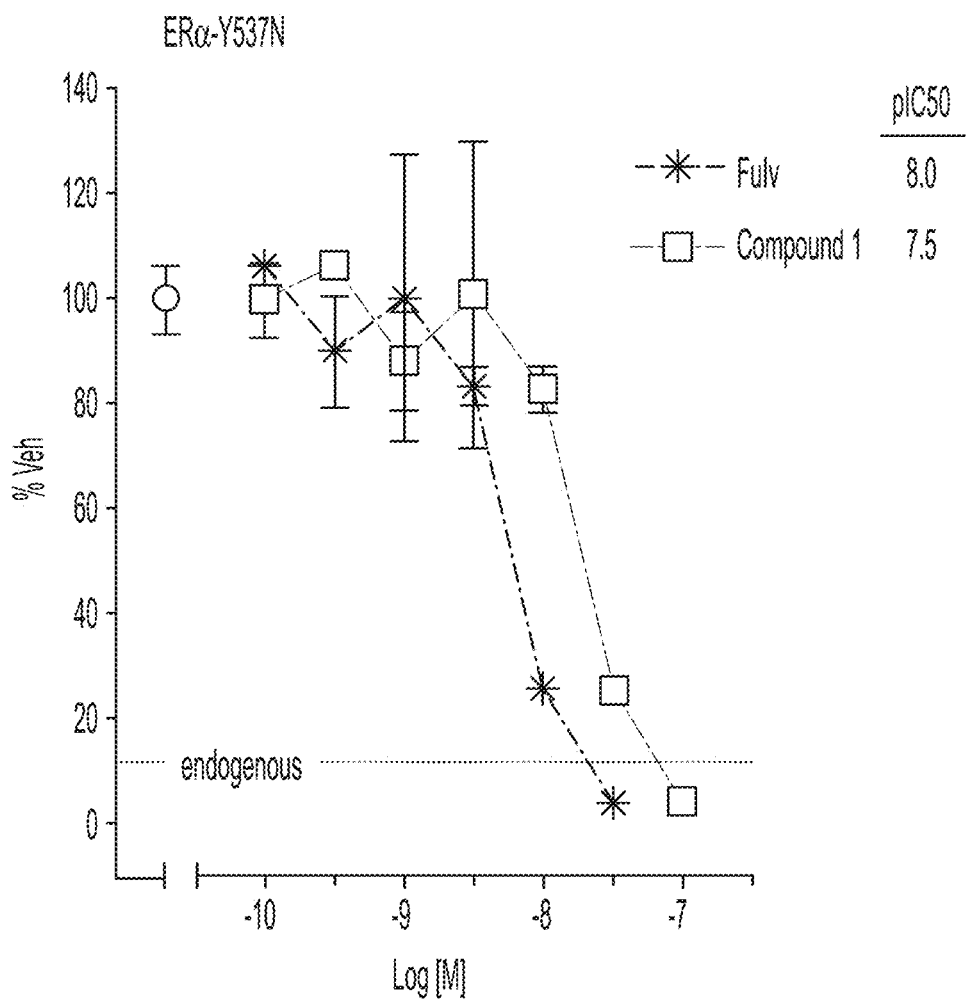
Figure 5F:
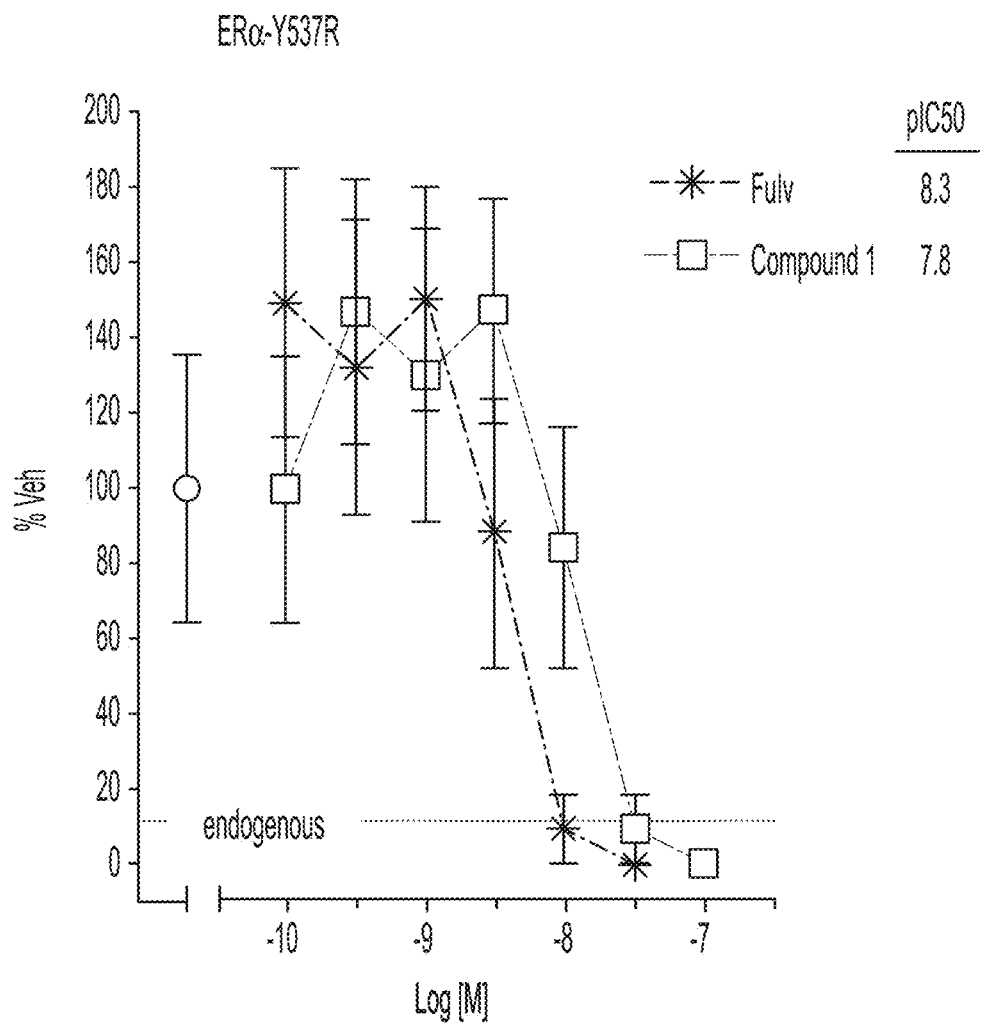

The present disclosure further offers an insight that the unique ability of Compound 1 to function as an inhibitor of both AF1 and AF2 makes it particularly attractive for use in certain combination therapies. As illustrated in FIGS. 3A-3B (for CDK4/6 inhibitors) and FIGS. 4A-4B (for PIK3CA inhibitors), Compound 1, an estrogen receptor antagonist, and indeed a complete estrogen receptor antagonist, in combination with a secondary agent can substantially eliminate cell proliferation. The present disclosure encompasses the recognition that a combination of certain agents can beneficially be used to completely antagonize the estrogen receptor by inactivating both AF1 and AF2. Accordingly, in some embodiments, the present disclosure provides a method of treating a subject suffering from a cancer comprising administering a compound that is an inhibitor of activating function 2 and a secondary agent that is an inhibitor of activating function 1. In some embodiments, wherein the compound is an estrogen receptor antagonist selected from AZD9496, RAD-1901, ARN-810, endoxifen, Fulvestrant, and Compound 1. In some embodiments, the compound is selected from fulvestrant and Compound 1.

In some embodiments, the present disclosure provides a method of treating a patient or subject suffering from a cancer, the method comprising administering Compound 1 and a secondary agent selected from a CDK2, CDK4, CDK6, or CDK7 inhibitor. In some embodiments, the secondary agent is a CDK2 inhibitor. In some embodiments, the secondary agent is a CDK4 inhibitor. In some embodiments, the secondary agent is a CDK6 inhibitor. In some embodiments the secondary agent is a CDK7 inhibitor. In some embodiments, the secondary agent is a CDK4/6 inhibitor (i.e., inhibits one or both of CDK4 and CDK6). In some embodiments, the secondary agent is a CDK2/4/6 inhibitor (i.e., inhibits one or more of CDK2, CDK4 and CDK6).

In some embodiments, the secondary agent is a CDK4/6 inhibitor selected from palbociclib, ribociclib, abemaciclib, lerociclib, trilaciclib, and SHR6390. In some embodiments, the CDK 4/6 inhibitor is palbociclib. In some embodiments, the CDK4/6 inhibitor is ribociclib. In some embodiments, the CDK4/6 inhibitor is abemaciclib. In some embodiments, the CDK4/6 inhibitor is lerociclib. In some embodiments, the CDK4/6 inhibitor is trilaciclib. In some embodiments, the CDK 4/6 inhibitor is SHR6390.

In some embodiments, the present disclosure provides a method of treating a patient or subject suffering from a cancer, the method comprising administering Compound 1 and a secondary agent, wherein the secondary agent is a PIK3CA inhibitor. In some embodiments, the PIK3CA inhibitor is selected from alpelisib, taselisib, and LY3023414. In some embodiments, the PIK3CA inhibitor is alpelisib. In some embodiments, the PIK3CA inhibitor is taselisib. In some embodiments, the PIK3CA inhibitor is LY3023414.

In some embodiments, the present disclosure provides a method of treating a patient or subject suffering from a cancer, the method comprising administering Compound 1 and a secondary agent, wherein the secondary agent is an mTOR inhibitor. In some embodiments, the mTOR inhibitor is selected from sirolimus, temsirolimus, everolimus, and LY3023414. In some embodiments, the mTOR inhibitor is sirolimus. In some embodiments, the mTOR inhibitor is temsirolimus. In some embodiments, the mTOR inhibitor is everolimus. In some embodiments, the mTOR inhibitor is LY3023414.

Dosing

Figure 6:
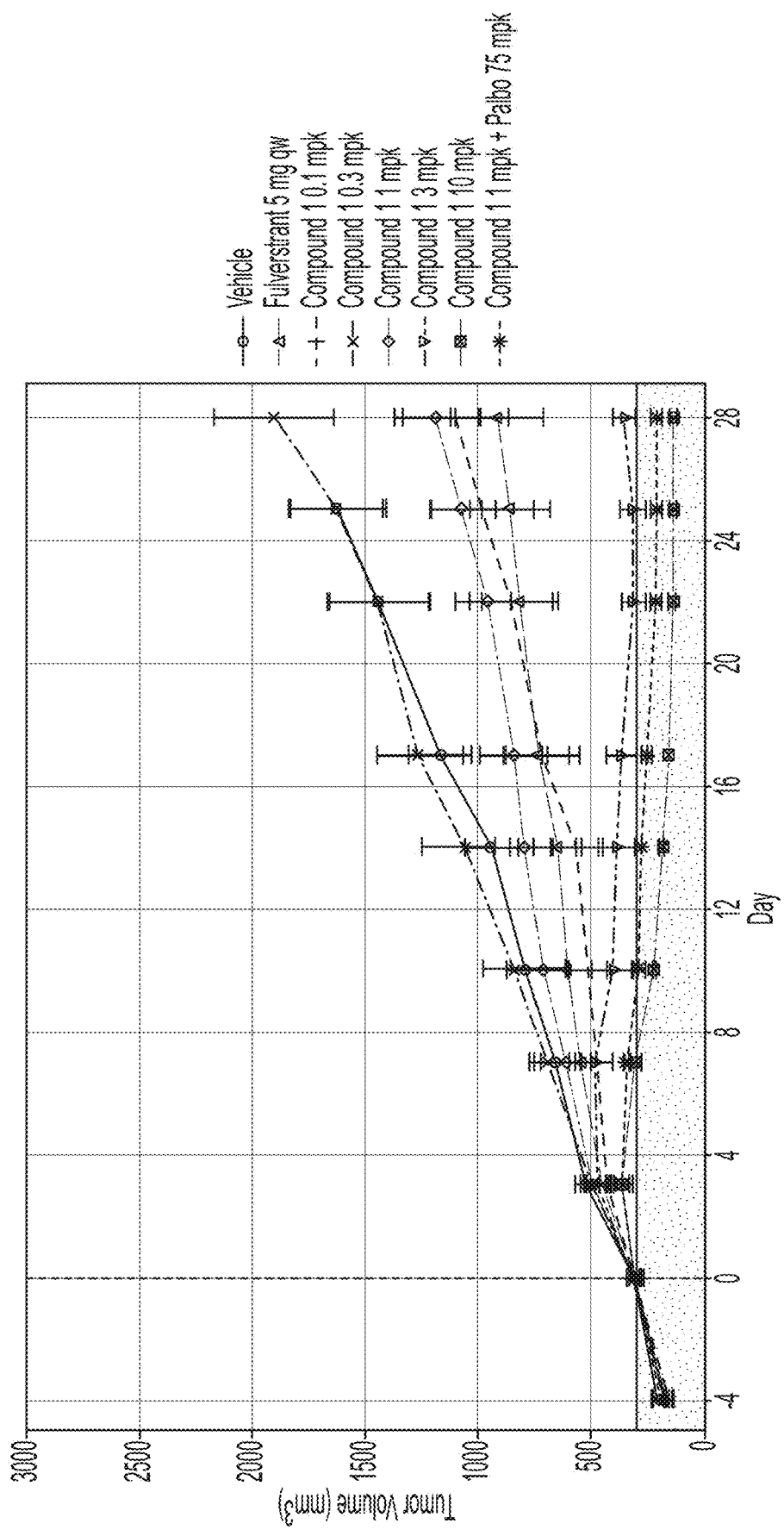
FIG. 6 is a scatter plot illustrating change in tumor volume for varying doses of Compound 1.
Figure 7A:
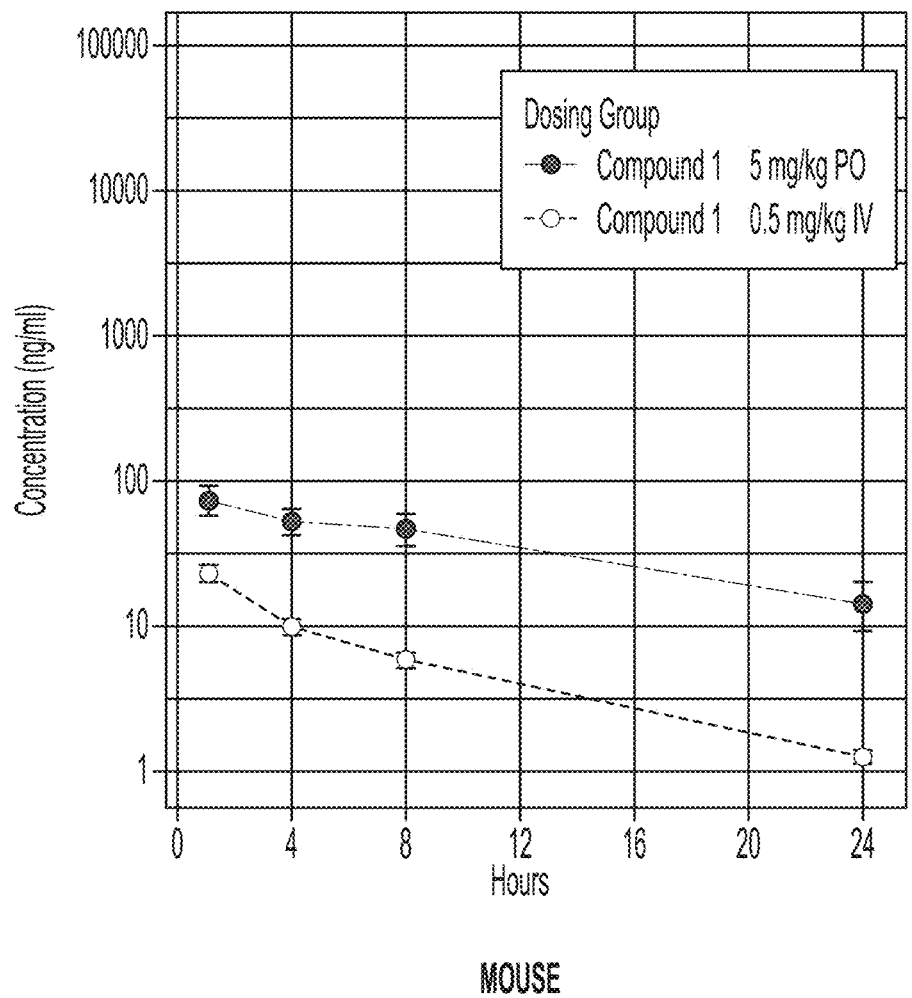
FIGS. 7A-7D are scatter plots measuring drug exposure (ng/ml) over time for mouse FIG. 7A), rat (FIG. 7B), dog (FIG. 7C), and monkey (FIG. 7D).
Figure 7B:
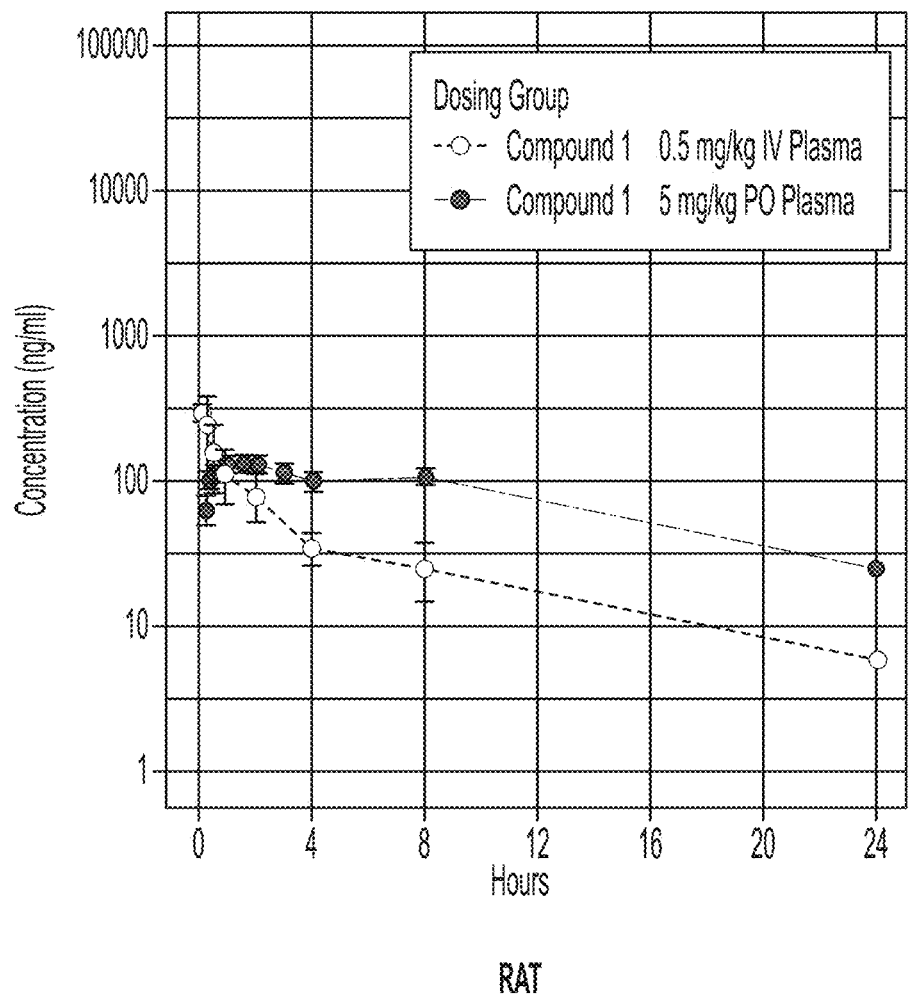
Figure 7C:
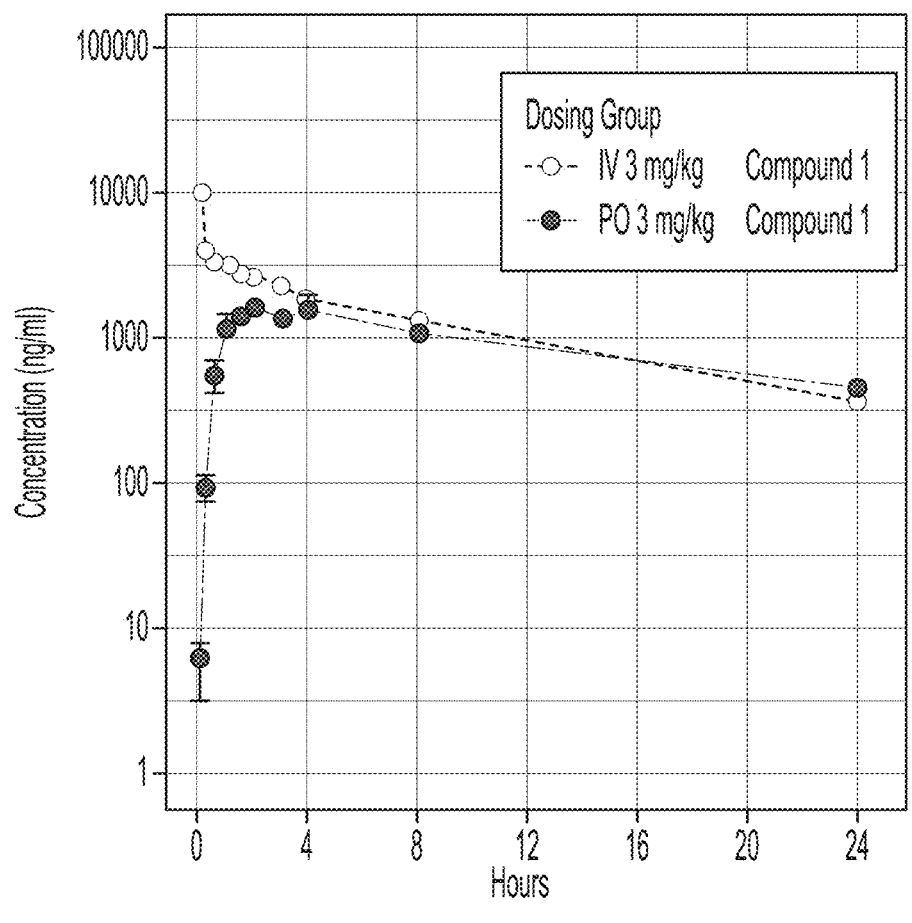
Figure 7D:
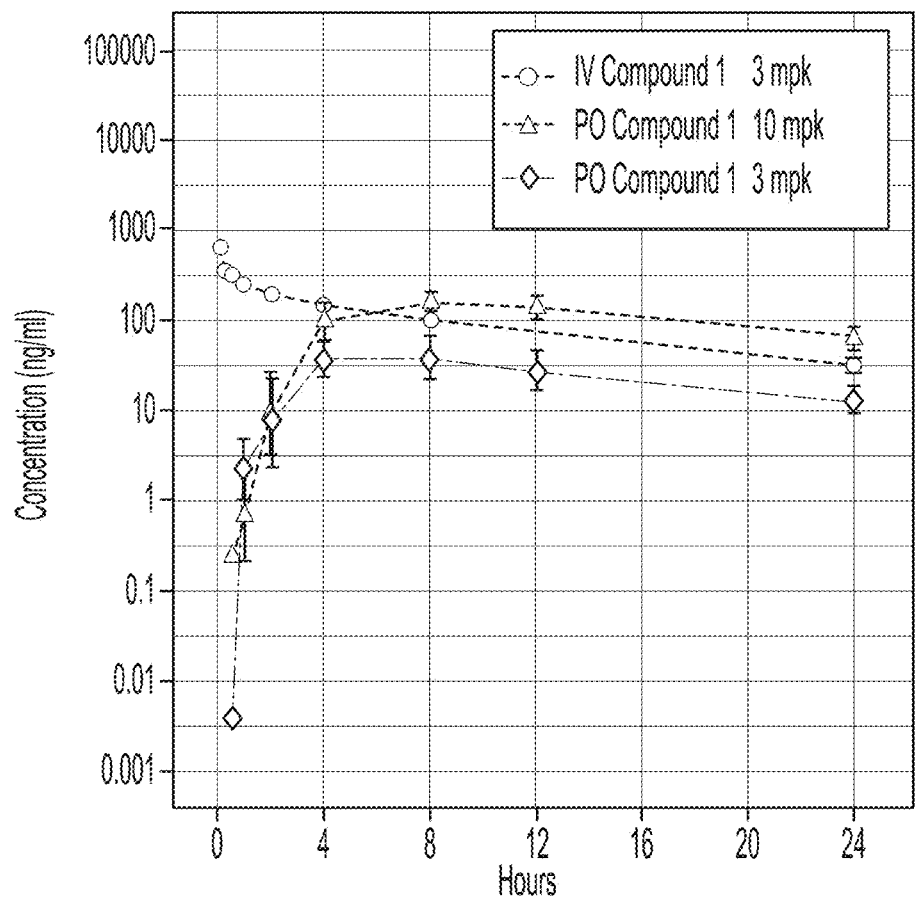

The present disclosure encompasses the recognition that certain disorders or conditions, e.g., cancer, can be effectively treated using amounts of active compound that is less than other compounds of similar activity. For example, as illustrated in FIG. 6, Compound 1 was found to reduce tumor volume more efficiently than other CERANs e.g., fulvestrant. Moreover, Compound 1 is suitable for oral administration, which is a benefit over other CERANs, e.g., fulvestrant, which must be administered parenterally.

Accordingly, the present disclosure provides a method of treating a patient or subject suffering from a cancer, the method comprising administering a composition comprising Compound 1. In some embodiments, the composition comprises Compound 1 and a pharmaceutically acceptable excipient, carrier, or diluent. Said composition may be administered orally, parenterally, by inhalation or nasal spray, topically (e.g., as by powders, ointments, or drops), rectally, buccally, intravaginally, intraperitoneally, intracisternally or via an implanted reservoir, depending on the severity of the condition being treated. Preferably, the compositions are administered orally, intraperitoneally or intravenously. In certain embodiments, provided compounds are administered orally or parenterally at dosage levels of about 0.01 mg/kg to about 50 mg/kg, of subject body weight per day, one or more times a day, to obtain the desired therapeutic effect.

Pharmaceutically acceptable compositions described herein may be orally administered in any orally acceptable dosage form including, but not limited to, capsules, tablets, aqueous suspensions or solutions. In such solid dosage forms the active compound may be admixed with at least one inert diluent such as sucrose, lactose or starch. Such dosage forms may also comprise, as is normal practice, additional substances other than inert diluents, e.g., lubricants and other tableting aids such a magnesium stearate and microcrystalline cellulose. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents. The active compounds can also be in micro-encapsulated form with one or more excipients as noted above.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings (i.e. buffering agents) and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions described herein may be administered in the form of suppositories for rectal or vaginal administration. These can be prepared by mixing the compounds of the present application with suitable non-irritating excipients or carriers that are solid at room temperature but liquid at body (e.g. rectal or vaginal) temperature and therefore will melt in the rectum or vaginal cavity to release the active compound. Such materials include cocoa butter, a suppository wax (e.g., beeswax) and polyethylene glycols.

In some embodiments, the composition is administered orally. In some embodiments, the composition is administered in an amount that is 30 mg/kg or less of the weight of the patient or subject. In some embodiments, the composition is administered in an amount that is 10 mg/kg or less of the weight of the patient or subject. In some embodiments, the composition is administered in an amount that is 10, 9, 8, 7, 6, 5, 4, 3, 2, or 1 mg/kg of the weight of the patient or subject. In some embodiments, the composition is administered in an amount that is 3 mg/kg or less of the weight of the patient or subject. In some embodiments, the composition is administered in an amount that is 1 mg/kg or less of the weight of the patient or subject. In some embodiments, the composition is administered in an amount that is 0.9, 0.8. 0.7, 0.6, 0.5, 0.4, 0.3, 0.2, or 0.1, mg/kg of the weight of the patient or subject. In some embodiments, the composition is administered in an amount that is 0.1 mg/kg of the weight of the patient.

In some embodiments, Compound 1 is administered as a unit dosage form. In some embodiments, Compound 1 is administered in the form of a capsule. In some embodiments, Compound is administered in the form of a tablet. In some embodiments, Compound 1 is administered as a suspension. In some embodiments, Compound 1 is administered as a solution.

In some embodiments, Compound 1 is administered as a daily dose (QD). In some embodiments, Compound 1 is administered as a twice daily dose (BID). In some embodiments, Compound 1 is administered every other day (QOD). In some embodiments, Compound 1 is administered as a weekly dose (QW). In some embodiments, Compound 1 is administered as a monthly dose (Q4W).

As illustrated in FIGS. 7A-7D, drug exposure (ng/ml) over time is high and even for mouse (FIG. 7A), rat (FIG. 7B), dog (FIG. 7C), and monkey (FIG. 7D) subjects.

Disorders or Conditions

The present disclosure also encompasses the recognition that Compound 1 advantageously can be used to treat metastasized cancers, e.g., cancers that have spread to the brain, bones, lungs, liver, or the central nervous system. As illustrated the table below, Compound 1, when administered in a single oral 300 mg/kg dose, is able to penetrate the blood brain barrier. Other estrogen receptor antagonists, e.g., fulvestrant, are unable to penetrate the blood-brain barrier in analogous quantities.

| Matrix | Group | Dose | Dose Unit | Concentration (ng/ml) |
|---|---|---|---|---|
| Plasma | Compound 1 10 mpk | 10 | mg/kg | 1919 |
| Plasma | Compound 1 30 mpk | 30 | mg/kg | 5558 |
| Brain | Compound 1 10 mpk | 10 | mg/kg | 2147 |
| Brain | Compound 1 30 mpk | 30 | mg/kg | 9708 |
| Brain | Fulvestrant 5 mg qw | 5 | mg | 501 |

Accordingly, the present disclosure provides a method of treating a patient or subject suffering from a cancer that has metastasized to the brain, bones, lungs, liver or the central nervous system, comprising administering Compound 1:

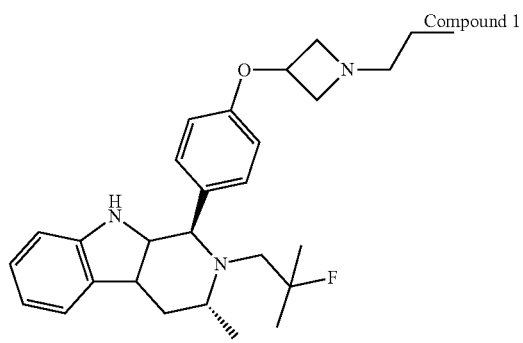 [SMILES: CCCN1CC(Oc2ccc([C@@H]3C4Nc5ccccc5C4C[C@@H](C)N3CC(C)(C)F)cc2)C1]

Compound 1

In some embodiments, the cancer includes one or more CNS tumors (e.g., metastases); in some embodiments, the cancer has metastasized to the brain, bones, lungs, or liver. In some embodiments, the cancer has metastasized to the central nervous system.

EXEMPLIFICATION

The Examples provided herein document and support certain aspects of the present disclosure but are not intended to limit the scope of any claim. Unless specifically presented in the past tense, inclusion in the Examples is not intended to imply that work described has been completed, or even performed. The following non-limiting examples are provided to further illustrate certain teachings provided by the present disclosure. Those of skill in the art, in light of the present application, will appreciate that various changes can be made in the specific embodiments that are illustrated in the present Examples without departing from the spirit and scope of the present teachings.

The following abbreviations may be used in the Examples below: aq. (aqueous); ACN (acetonitrile); CSA (camphorsulfonic acid); d (day or days); DCM (dichloromethane); DEA (diethylamine); DHP (dihydropyran); DMF (N,N-dimethylformamide); DIPEA (N,N-diisopropylethylamine); DMAP (4-dimethylaminopyridine); DMSO (dimethyl sulphoxide); EA (ethyl acetate); ee (enantiomeric excess); equiv. (equivalent); ethanol (EtOH); h (hour or hours); Hex (hexanes); HPLC (high-performance liquid chromatography); IPA (isopropyl alcohol); KHMDS (potassium bis(trimethylsilyl)amide); LAH (lithium aluminum hydride); LCMS (liquid chromatography-mass spectrometry); LDA (lithium diisopropylamide); LiHMDS (lithium bis(trimethylsilyl)amide); MeOH (methanol); min (minute or minutes); NMR (nuclear magnetic resonance); Pd/C (palladium on carbon); PPh₃O (triphenylphosphine oxide); Pt/C (platinum on carbon); rb (round-bottomed); Rf (retention factor); rt or RT (room temperature); SM (starting material); TEA (triethylamine); THF (tetrahydrofuran); THP (tetrahydropyran); TLC (thin layer chromatography); TsOH (p-toluenesulfonic acid or tosylic acid); and UV (ultraviolet).

Example 1

Synthesis of Compound 1

The complete synthesis of Compound 1 is provided in PCT App. Pub. No. WO 2017/059139, which is incorporated herein by reference and repeated below.

Preparation of 4-((1-propylazetidin-3-yl)oxy)benzaldehyde

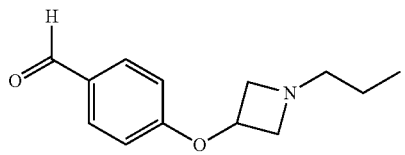 [SMILES: CCCN1CC(Oc2ccc(C=O)cc2)C1]

Step 1: Preparation of 1-propionylazetidin-3-one

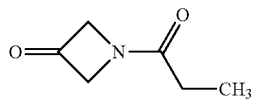

The compound 3-azetidinone hydrochloride (10.000 g, 93.0 mmol, 1.0 equiv.), anhydrous 1,2-dichloroethane (200 mL) and diisopropylethylamine (38.9 mL, 223 mmol, 2.4 equiv.) were added to a round bottom flask (500 mL) to provide a light yellow suspension. The suspension was sonicated for 1 h and then cooled to −10° C. (dry-ice/MeOH) for 10 min. Propionyl chloride (9.8 mL, 112 mmol, 1.2 equiv.) was added dropwise to the cooled suspension to provide an orange solution. The reaction was removed from the bath and stirred at room temperature for 16 h. The solvent was removed to provide a semi-solid. The semi-solid was suspended into EA (300 mL) and the suspension was filtered. The solid was rinsed with EA (2×100 mL). TLC analysis (10% MeOH/DCM, KMnO₄ stain/Heat) indicated there were three spots: Rf: 0.2, 0.5, 0.7. TLC (50% EA/Hex, KMnO₄ stain/Heat) indicated there were two spots: Rf: 1, 0.3. The filtrate was concentrated, adsorbed onto silica gel (25 g) and chromatographed through silica gel (100 g cartridge) with DCM (5 min) then 0-10% MeOH over 15 min. The product came off early from the column in DCM and continued to elute from the column with up to 10% MeOH. TLC in both solvent systems was carried out to determine if any propionyl chloride was present in early fractions. Fractions containing product were pooled and concentrated to afford the title compound as a yellow liquid (11.610 g, 98.2%).

¹H NMR (300 MHZ, CDCl₃) δ:4.80 (d, J=5.6 Hz, 4H), 2.29 (q, J=7.5 Hz, 2H), 2.01 (s, 3H), 1.18 (t, J=7.5 Hz, 3H).

Step 2. Preparation of 1-propylazetidin-3-ol

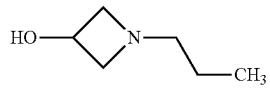

Lithium aluminum hydride (10.397 g, 273.9 mmol, 3.0 equiv.) was suspended into THF (200 mL) and cooled in an ice bath. A solution of 1-propionylazetidin-3-one (11.610 g, 91.3 mmol, 1.0 equiv.) in THF (100 mL) was added dropwise to the reaction mixture via a pressure equalizing addition funnel over 30 min. The addition funnel was removed. The flask was then fitted with a condenser and the reaction was heated at reflux in an oil bath at 75° C. for 16 h. The reaction was cooled in an ice bath for 20 min and sodium sulfate decahydrate (Glauber's salt, 25 g) was added in small portions over 20 min. After complete addition, the mixture was stirred at room temperature for 2 h. The mixture was filtered through a bed of Celite® (2 cm) and the solids rinsed with EA (2×250 mL). The clear solution was concentrated to a pale yellow liquid (9.580 g, 91.1%). NMR indicated the presence of THF and EA. This material was used without further purification in the preparation of the compounds of the examples below.

¹H NMR (300 MHz, CDCl₃) δ:4.39 (pent, J=6 Hz, 1H), 3.62-3.56 (m, 2H), 2.90-2.85 (m, 2H), 2.41 (t, J=7.5 Hz, 2H), 1.34 (hextet, J=7.2 Hz, 2H), 0.87 (t, J=7.8 Hz, 3H).

Preparation of (R)-1-(1H-indol-3-yl)-N—((R)-1-phenylethyl) propan-2-amine:

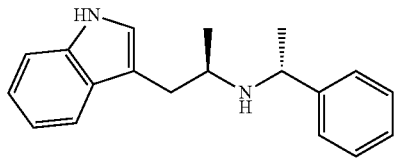 [SMILES: C[C@H](Cc1c[nH]c2ccccc12)N[C@H](C)c1ccccc1]

Indole-3-acetone (25.0 g, 144 mmol, 1.0 equiv.) was added to a solution of (R)-(+)-1-phenylethylamine (23.0 mL, 181 mmol, 1.3 equiv.) in dichloromethane (600 mL) under N₂ at 25° C. and the mixture was allowed to stir for 1 hr. The reaction was cooled to 0-5° C. and sodium triacetoxyborohydride (100 g, 472 mmol, 3.3 equiv.) was added over 30 minutes via powder addition funnel to the ice cooled solution. The orange solution was stirred for 1 h at 0° C. and then was allowed to warm to RT. The reaction was stirred at RT for 19 h. At this time, ESI+ indicated that no indole starting material was present. Saturated NaHCO₃ solution (100 mL) was added in 5 mL portions over 15 min at 10° C. with vigorous stirring. The solution was stirred for 15 min and sat. Na₂CO₃ solution (200 mL) was added over 15 minutes. Solid K₂CO₃ (9 g) was added in 3 g portions at which point the aqueous layer was pH 12 and bubbles had stopped forming. The layers were filtered and separated. The red organic layer was washed with sat. aq. NaHCO₃ (2×100 mL). The aqueous layers were combined and extracted with DCM (2×100 mL). The combined organic layers were dried over Na₂SO₄, filtered and concentrated to give the crude product (49 g). TLC (90:10 DCM: MeOH) showed four spots (Rf=0.63, 0.50, 0.16, 0.26), two of which were separated diastereomeric major products (Rf=0.16 and 0.26). The crude was adsorbed onto silica gel and purified via flash chromatography (330 g cartridge, 0-100%

EA:Hex). Fractions containing the R,R diastereomer were pooled and purified a second time with the same flash chromatography conditions to afford 24 g of product (~82% ee). Previous successful separation was achieved by a silica gel:crude ratio of 40:1, so the mixture was divided into 3 portions and separated on 3×330 g silica gel cartridges (0-40% EA/Hex for 20 min, isocratic 40% EA/Hex 40 min). All fractions containing the desired product were >99% diastereomerically pure. Pure fractions were concentrated and pooled to yield (R)-1-(1H-indol-3-yl)-N—((R)-1-phenylethyl)-propan-2-amine as an orange semi-solid (11.91 g, 29.6%).

$^1$H NMR (CDCl$_3$, 300 MHZ) R,R diastereomer: δ 0.96 (d, J=6.6 Hz, 3H), 1.30 (d, J=6.6 Hz, 3H), 2.68 (q, J=7.2 Hz, 1H), 2.97 (m, 2H) 4.00 (q, J=6.3 Hz, 1H), 7.43-6.97 (m, 10H), 7.96 (br s, 1H). R,S diastereomer: δ 1.11 (d, J=5.7 Hz, 3H), 1.30 (d, J=5.4 Hz, 3H) 2.80 (m, 3H), 3.92 (q, J=6.9 Hz, 1H), 6.93-7.40 (m, 10H), 8.13 (br s, 1H); the aromatic region was difficult to distinguish from the R,R diastereomer due to lack of purity.

LCMS: ES+ [M+H]+ 279.0.

Preparation of (2R)-1-(1H-indol-3-yl) propan-2-amine

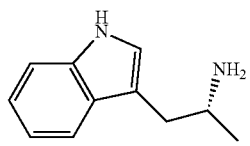

The compound (R)-1-(1H-indol-3-yl)-N—((R)-1-phenylethyl) propan-2-amine (11.91 g, 42.8 mmol, 1.0 equiv.) was dissolved in methanol (250 mL) and added to a 2 L Parr bottle and the solution was sparged with N$_2$ for 10 min. 20% Pd(OH)2 on carbon wet with water (10.71 g, 76.3 mmol, 1.8 equiv.) was added and the bottle was pressurized with 50 psi of hydrogen and shaken in a Parr apparatus for 22 h, LCMS analysis indicated that the reaction was completed. The suspension was filtered through Celite® and concentrated to remove MeOH. The crude was dissolved into DCM and washed with saturated Na$_2$CO$_3$ solution (50 mL) and the aqueous layer was extracted with DCM (2×50 mL). The organic layers were combined, dried, and concentrated to yield (2R)-1-(1H-indol-3-yl) propan-2-amine as a light brown solid that did not require further purification (6.68 g, 89.6%).

$^1$H NMR (CDCl$_3$, 300 MHZ) δ 1.17 (d, J=6.6 Hz, 3H), 2.66 (dd, J=8.4, 14.7 Hz, 1H), 2.88 (dd, J=5.4, 14.1 Hz, 1H), 3.27 (sextet, J=1.5 Hz, 1H), 7.05-7.22 (m, 3H), 7.37 (d, J=7.5 Hz, 1H), 7.62 (d, J=8.7 Hz, 1H), 8.00 (br s, 1H).

LCMS: ES+ [M+H]+ 174.9.

Preparation of 2-fluoro-2-methylpropanol

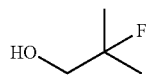

Methyl 2-fluoro-2-methylpropionate (5.01 g, 40.5 mmol, 1.0 equiv.) was added dropwise over 15 min to a stirred suspension of lithium aluminum hydride (2.50 g, 65.9 mmol, 1.6 equiv.) in anhydrous diethyl ether (100 mL) cooled in an ice bath. After 2 hours, 2.0 mL water, 2.0 mL 15% w/v NaOH, and 5.0 mL water were added sequentially dropwise. After 15 min, the white suspension was diluted with DCM, gravity filtered through Celite®, and the solids were washed with DCM. The filtrate was concentrated (200 mbar, 25° C.) to afford 2-fluoro-2-methylpropanol as a colorless oil (2.09 g, 56.1%).

$^1$H NMR (300 MHz, CDCl$_3$) δ 1.34 (d, J=21.3 Hz, 6H), 1.95 (br t, 1H), 3.56 (dd, J=6.6, 20.7 Hz, 2H).

Preparation of 2-fluoro-2-methylpropyl trifluoromethanesulfonate

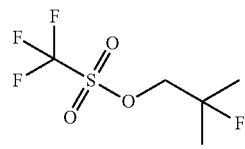

Trifluoromethanesulfonic anhydride (5.0 mL, 29.7 mmol, 1.3 equiv.) was added dropwise to a 0° C. solution of 2-fluoro-2-methylpropanol (2.090 g, 22.7 mmol, 1.0 equiv.) and 2,6 lutidine (3.40 mL, 29.4 mmol, 1.3 equiv.) in DCM (25 mL) over 30 minutes. After 2 hours, the red solution had turned light brown. TLC (20:80 EA: Hex, KMnO$_4$ stain) indicated that the starting material was not present. The reaction mixture was washed with 1M HCl solution (2×20 mL) and sat. NaHCO$_3$ solution (2×20 mL). The aqueous layers were each back extracted with DCM (20 mL). The combined organic layers were dried with Na$_2$SO$_4$, filtered and concentrated under reduced pressure (150 mbar, 25° C.) to afford 2-fluoro-2-methylpropyl trifluoromethanesulfonate as a red oil (4.39 g, 86.3%).

$^1$H NMR (300 MHz, CDCl$_3$) δ 1.46 (d, J=20.4 Hz, 6H), 4.41 (d, J=18.6 Hz, 2H). $^{19}$F NMR (282 MHZ, CDCl$_3$) δ −147.1, −74.5.

Preparation of (R)—N-(1-(1H-indol-3-yl) propan-2-yl)-2-fluoro-2-methylpropan-1-amine

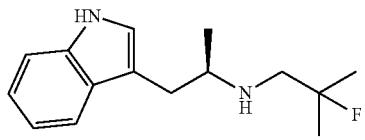 [SMILES: C[C@H](Cc1c[nH]c2ccccc12)NCC(C)(C)F]

The compound 2-fluoro-2-methylpropyl trifluoromethanesulfonate (9.587 g, 42.8 mmol, 1.1 equiv.) (solution in DCM, 16% DCM by wt %, 11.4384 g) was added to a solution of (2R)-1-(1H-indol-3-yl) propan-2-amine (6.680 g, 38.3 mmol, 1.0 equiv.), anhydrous 1,4-dioxanes (60.000 ml, 701.4 mmol, 18.3 equiv.), and freshly-distilled diisopropylethylamine (8.500 ml, 48.8 mmol, 1.3 equiv.). The dark brown solution was heated at 90° C. for 3 hours. After 3 h, LCMS indicated that a small amount of indolamine starting material was still present. TLC (10% MeOH/DCM) indicated triflate (Rf=0.54) had been used up. NMR of unused triflate SM (286-30) indicated the triflate had not decomposed overnight, so another 0.1 equiv (0.9883 g, 13% DCM wt %, 0.8563 g triflate SM) was added and the reaction was heated for 2 h at 90° C. LCMS indicated the reaction had completed and TLC (10% MeOH/DCM) showed one spot (Rf=0.24) (TLC with 50% EA/Hex, 1 streaked spot Rf<=0.12, another spot at Rf=0). EtOAc (50 mL) was added and the solution was washed with NaHCO$_3$ (2×50 mL) and the combined aqueous layer was washed with EtOAc (50 mL). The combined organic extracts were dried over Na$_2$SO$_4$ and concentrated under reduced pressure. The crude (brown oil, 14.8 g) was purified via flash silica chromatography (240 g cartridge, 0-100% EA/Hex). The desired product eluted as a long tailing peak. Pure fractions were concentrated to yield (R)—N-(1-(1H-indol-3-yl) propan-2-yl)-2-fluoro-2-methylpropan-1-amine (4.211 g, 17.0 mmol) as a dark yellow oil.

$^1$H NMR (300 MHZ, CDCl$_3$) δ 1.10 (d, J=6.3 Hz, 3H), 1.34 (dd, J=3.0, 21.9 Hz, 6H), 2.68-2.95 (m, 4H), 3.02 (sextet, J=6.6 Hz, 1H), 7.05 (d, J=2.4 Hz, 1H), 7.26-7.11 (m, 2H), 7.36 (d, J=6.9 Hz, 1H), 7.62 (d, J=7.5 Hz, 1H), 8.18 (br s, 1H). $^{19}$F NMR (282 MHZ, CDCl$_3$) δ −144.2. m/z: ES+ [M+H]+ 249.0.

Preparation of Compound 1

4-((1-propylazetidin-3-yl)oxy)benzaldehyde (0.096 g, 0.4 mmol, 1.3 equiv.) was added to a solution of (R)—N-(1-(1H-indol-3-yl) propan-2-yl)-2-fluoro-2-methylpropan-1-amine (0.070 g, 0.3 mmol, 1.0 equiv.) in anhydrous toluene (1.50 mL) and glacial acetic acid (0.100 mL, 1.7 mmol, 6.2 equiv.). Molecular sieves were added and the solution was stirred under N$_2$ in the dark at 80° C. for 8 hours. The reaction solution was diluted in DCM, filtered, and washed with saturated Na$_2$CO$_3$ solution. The aqueous layer was extracted with DCM and the combined organic layers were dried over Na$_2$SO$_4$. The solution was filtered and concentrated. The residue was dissolved into acetonitrile (2 mL) and filtered through a syringe filter before purification via prep LC (40 to 90% ACN:H$_2$O over 18 min, followed by isocratic 90% ACN for 7 min). Pure fractions were concentrated and dried to afford (1R,3R)-2-(2-fluoro-2-methylpropyl)-3-methyl-1-(4-((1-propylazetidin-3-yl)oxy)phenyl)-2,3,4,9-tetrahydro-1H-pyrido[3,4-b]indole as a white powder.

Example 2

Estrogen Receptor Protein Level Assay

Figure 2:
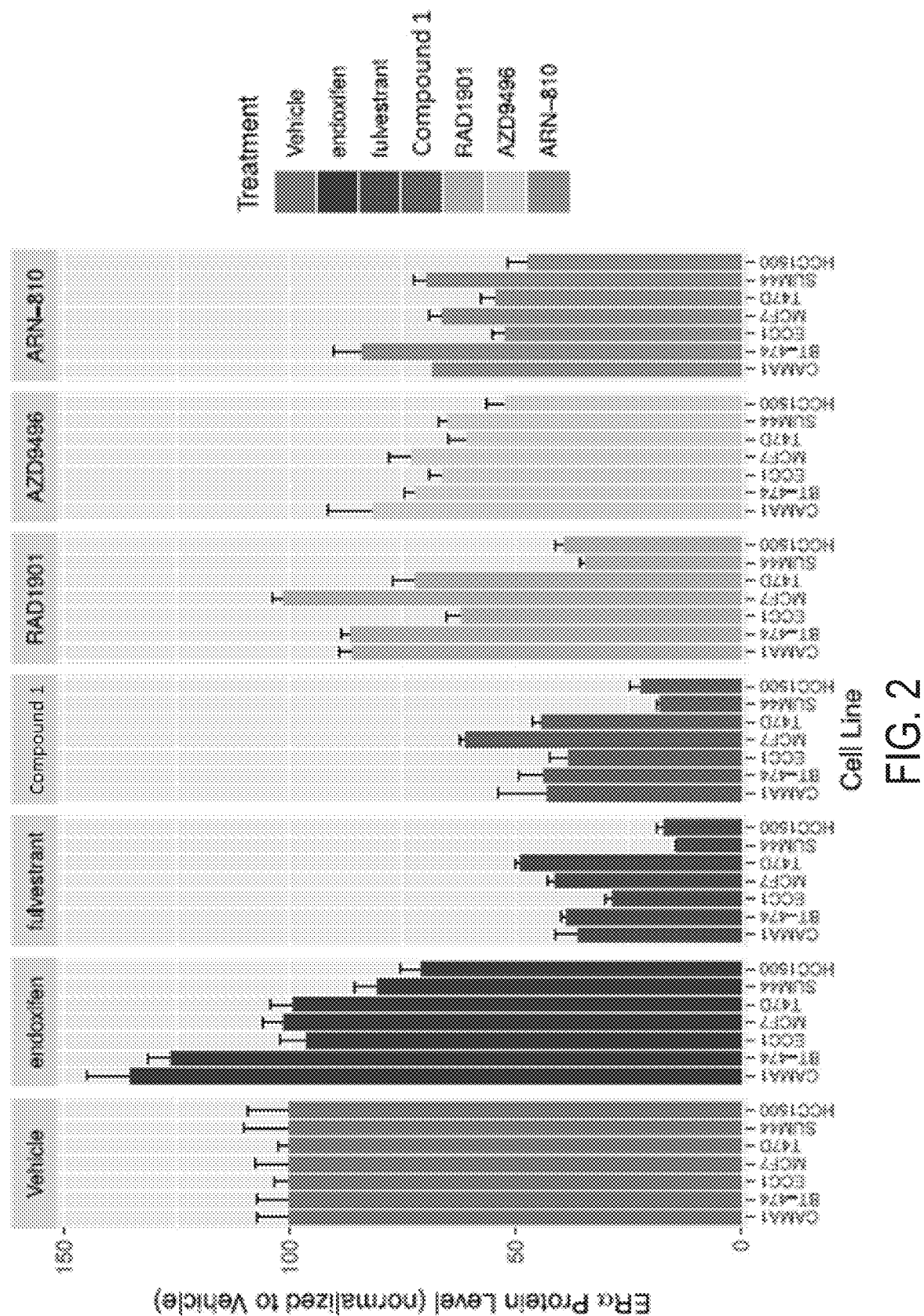
FIG. 2 is a chart measuring degradation of the estrogen receptor protein across multiple cell lines for multiple estrogen receptor antagonists.

The present Example describes assessment of various compounds (ARN-810, AZD9496, Compound 1, Endoxifen, and Fulvestrant) on ERα protein level in a variety of cell lines. Depending on the cell type, 90,000-500,000 cells per well were previously plated into each well of a 12-well dish and incubated in phenol red-free media containing 5% charcoal dextran stripped fetal bovine serum (stripped FBS) (HyClone) for at least 24 hours. Cells were treated with 300 nM antiestrogen for 4 hours in serum-free medium and lysates subsequently lysed with RIPA buffer supplemented with protease and phosphatase inhibitors (ThermoFisher Scientific). Whole protein extracts were separated on 10% SDS-PAGE TGX gels and transferred to nitrocellulose membranes (BioRad). Blots were incubated mouse monoclonal anti-ERα, either D12 (#sc-8005, SantaCruz Biotechnology) or SP1 (#MA5-14501, ThermoFisher Scientific). β-actin monoclonal antibodies (#MA5-15739 or #MA5-16410 (ThermoFisher Scientific) or #sc-47778 (SantaCruz Biotechnology)) were used as loading controls. Blots were incubated with appropriate secondary antibodies conjugated to horse radish peroxidase (ThermoFisher Scientific). Signal was detected with Super Signal Femto chemiluminescent reagent (ThermoFisher Scientific). Results are depicted in FIG. 2. As can be seen, all compounds other than Endoxifen showed significant ability to reduce ER protein level in most cell lines; Compound 1 and Fulvestrant were most effective at reducing ER protein level, and showed comparable activity in this respect.

Example 3

Cell Proliferation Assays

The present Example describes assays that assess impact of tested compounds on human MCF-7 cells, which are a human ER$^+$ breast cancer cell line. Specifically, 1000 MCF-7 cells (Cheryl Walker, Baylor College of Medicine) per well were plated into a 96-well plate in phenol red-free media (ThermoFisher Scientific) containing 5% stripped FBS. At least 4 hours later cells were treated with antiestrogens and media was diluted to 2.5% stripped FBS in the presence of 100 pM E2 for 6-8 days. Proliferation was measured using CyQuant fluorescent DNA-binding dye kit (ThermoFisher Scientific) using 1:200 GR dye and reading fluorescence at 485 nm excitation and 538 nm.

Example 4

Transient Transfection of Estrogen Receptors and Variants

Figure 9:
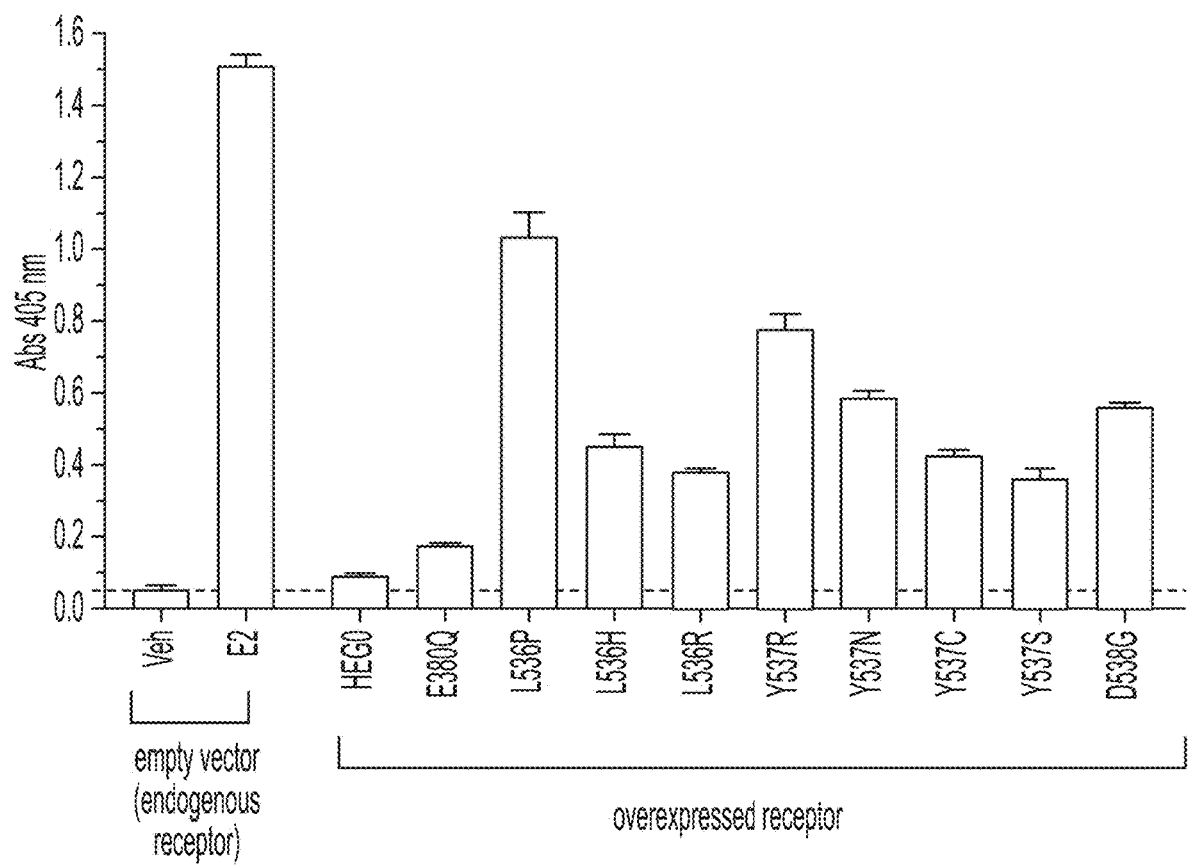
FIG. 9 is a bar graph illustrating that mutant ERs increase ligand-independent alkaline phosphatase activity (AP) in Ishikawa endometrial cancer cells.
Figure 10:
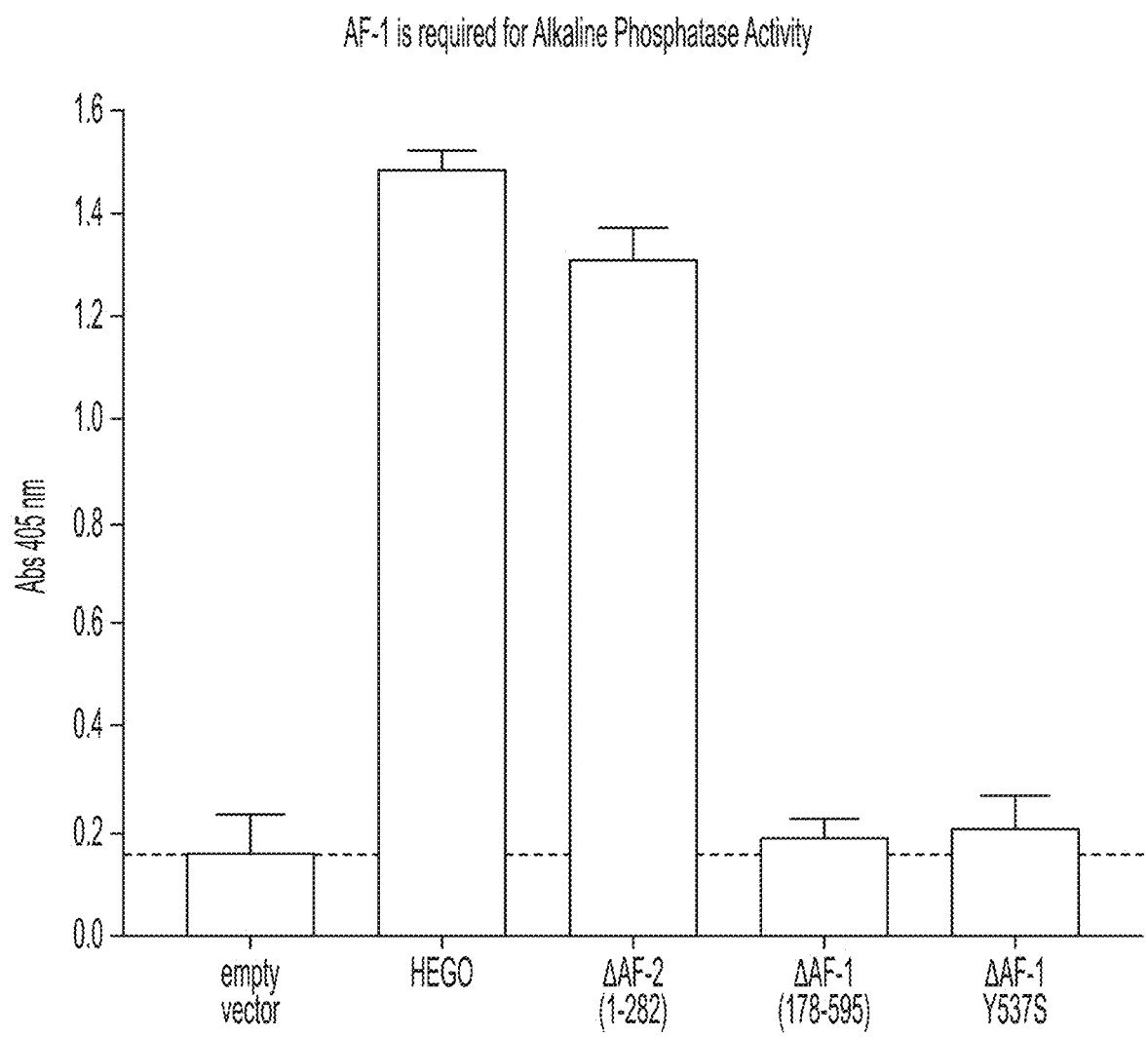
FIG. 10 is a bar graph illustrating that activation domain 1 (AF1) of the ER is required for AP activity.

The present Example describes studies in which certain estrogen receptor constructs were transfected into Ishikawa cells, which are a human endometrial cancer cell line, endogenous alkaline phosphatase is assayed. 15,000 Ishikawa cells per well were plated into a 96-well plate in phenol-red media containing 5% stripped FBS. At the time of plating, cells in each well were transiently transfected with 75-100 ng of an estrogen receptor construct (or empty vector, pSG5) using Lipofectamine LTX (ThermoFisher Scientific). Approximately 4 hours later, cells were treated with indicated amount of anti-estrogen (in the absence of E2), or 500 pM E2 (FIG. 9), and media was diluted to 2.5% stripped FBS. Cells were incubated for 3 days, media removed, and plates frozen at −80° C. Thawed plates were incubated with p-nitrophenyl phosphate (ThermoFisher Scientific), which is a chromogenic substrate of AP and therefore reveals AP activity levels. After 40-80 minutes at 40° C., absorbance was read at 405 nm.

Compound 1 has ER Antagonist, and not Agonist, Activity

Figure 1B:
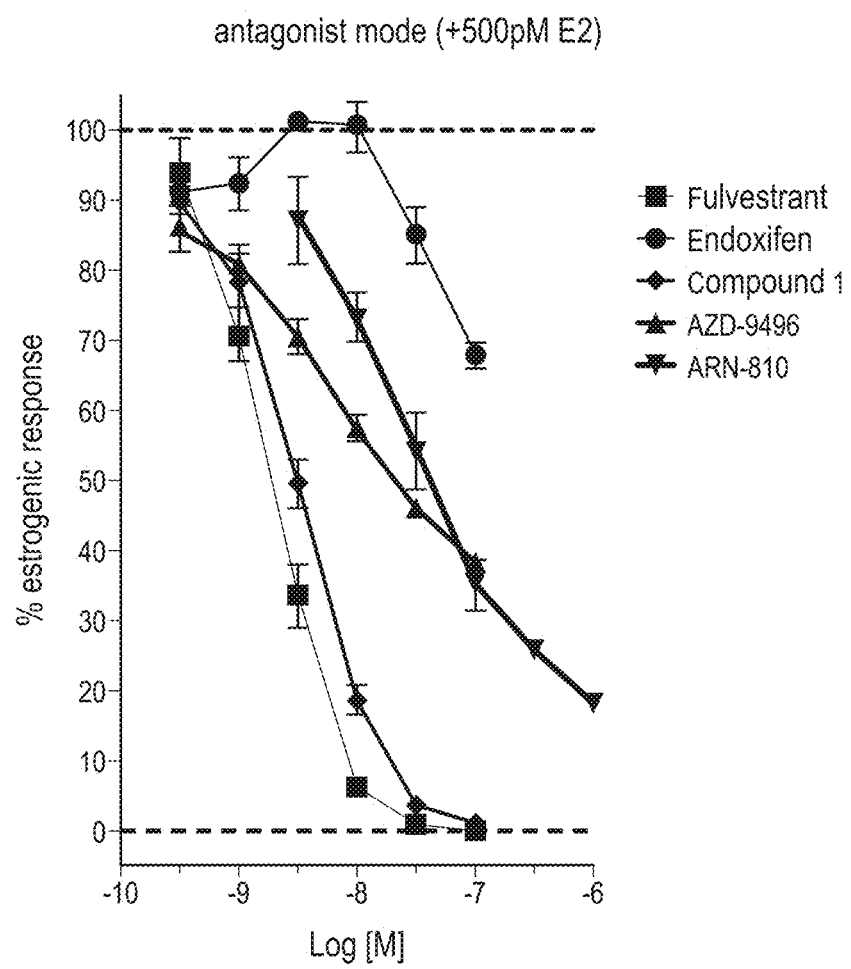
FIG. 1B is a scatter plot measuring percent of estrogenic response as a function of Log [M] for certain estrogen receptor antagonist compounds where estrogen has been added.

AP activity of endogenous wild type ER in un-transfected Ishikawa cells was assayed as described above. Cells were treated with indicated compound (ARN-810, AZD-9496, Compound 1, Endoxifen, or Fulvestrant) alone (agonist mode), or in the presence of 500 pM 17β-estradiol (E2) (antagonist mode). Results are presented in FIG. 1A (agonist mode) and FIG. 1B (antagonist mode). As can be seen, all compounds showed meaningful antagonist activity, with Compound 1 and Fulvestrant being most potent. All compounds other than Compound 1 and Fulvestrant also showed significant agonist activity.

Certain Mutant ERs Increase Ligand-Independent ER Activity

Wild type ER (HEGO), empty vector (pSG5) or indicated LBD mutant ER was transiently transfected into Ishikawa cells as described above. Only the empty vector was treated with 500 pM 17β-estradiol (E2). 72 hours later, cells were assayed for AP activity. Results are presented in FIG. 9. Bars represent mean absorbance at 405 nm from triplicate wells, +s.e.m. As can be seen, various of the tested ER mutants were observed to be "activating mutants" in that they showed more activity than did the wild type ER when ligand was not present.

Activation Domain 1 (AF1) is Required for Ligand-Independent Activity Observed with Certain ER Mutants AF1Wild type ER (HEGO, AA 1-595), empty vector (pSG5) or indicated ER missing the activation domain 2 ("AF2") (AA 1-282) or activation domain 1 ("AF1") (AA 178-595, with and without Y537S mutation), was transiently transfected into Ishikawa cells as described above. 72 hours later, cells were assayed for AP activity. Bars represent mean absorbance at 405 nm from quadruplicate wells, +s.e.m. As can be seen, F1AF1 is required for ligand-independent ER activity that is observed when the ER is truncated (ΔΔF2), even in the presence of the activating Y537S mutation (ΔΔF1/Y5372).

Compound 1 Inhibits Activity of Ligand-Independent ER Mutants

Wild type ER or an indicated ER variant transiently transfected into Ishikawa cells as described above, and activity was assayed in the presence of Compound 1 or fulvestrant. Results are presented in FIGS. 5A-5F (each of FIG. 5A to 5F reports a particular cell line, as indicated in each figure. Points represent mean AP activity normalized to vehicle, +/−s.e.m. from duplicate wells. Dose response curves of Compound 1 and Fulvestrant were fit using the least squares fit method and pIC50 (−Log $IC_{50}$) were calculated using a variable slope sigmoid dose-response model. Line represents the normalized AP activity of the endogenous receptor (transfected with empty vector (pSG5)). As can be seen, Compound 1 inhibited activity of each of the ligand-independent ER mutants with an $IC_{50}$ comparable to that of fulvestrant.

Figure 8A:
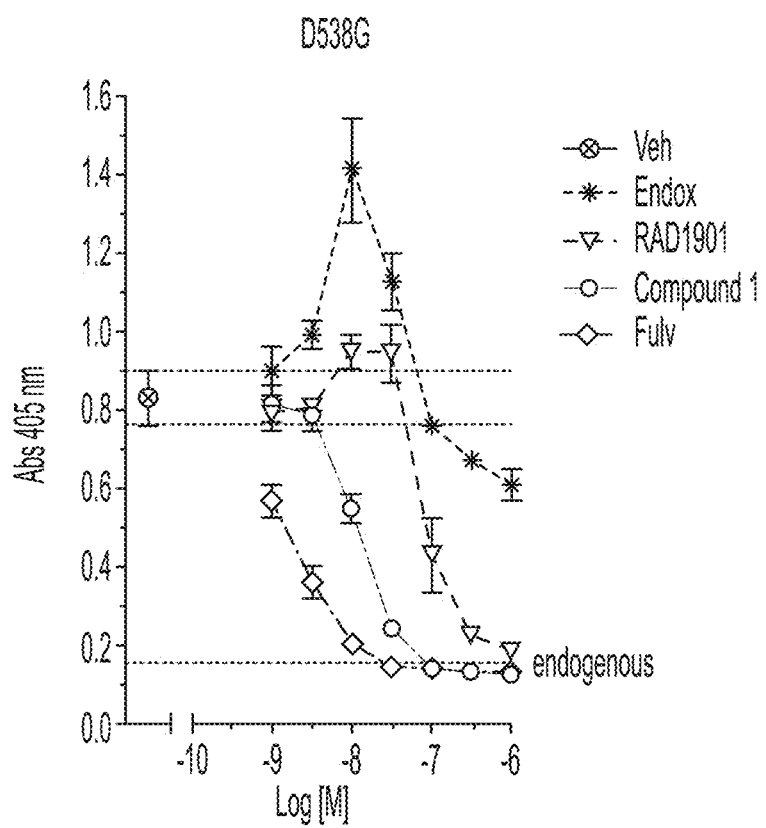
FIGS. 8A-8D are scatter plots illustrating the decreased in estrogen concentration across different cell lines.
Figure 8B:
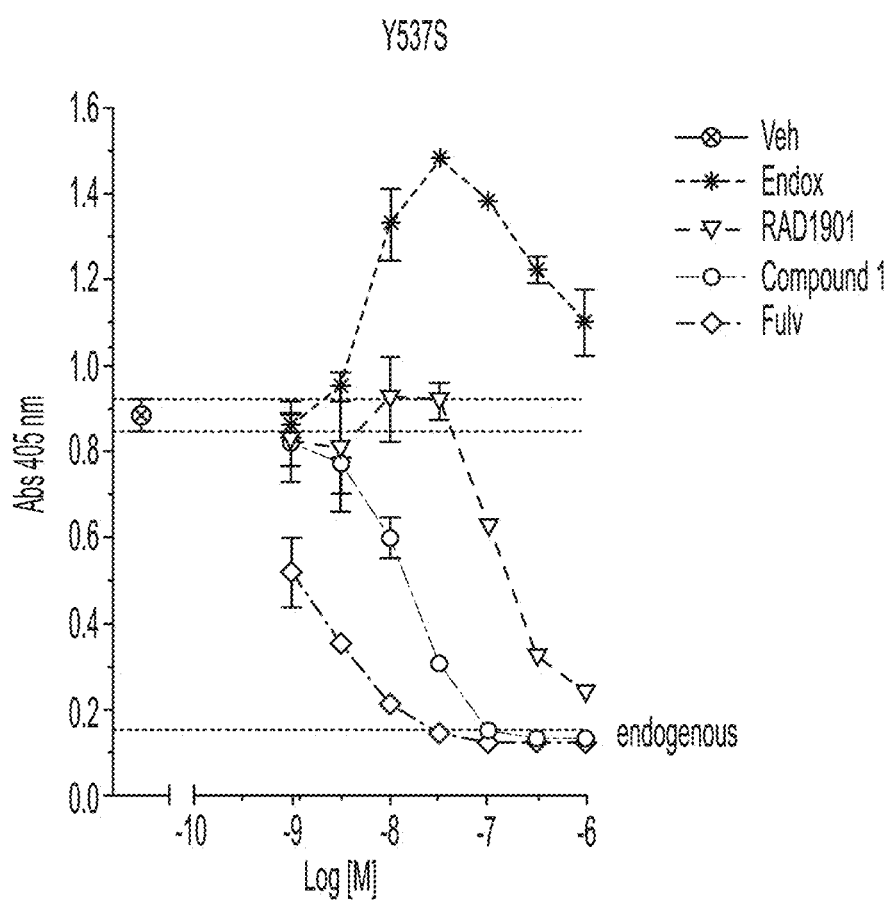
Figure 8C:
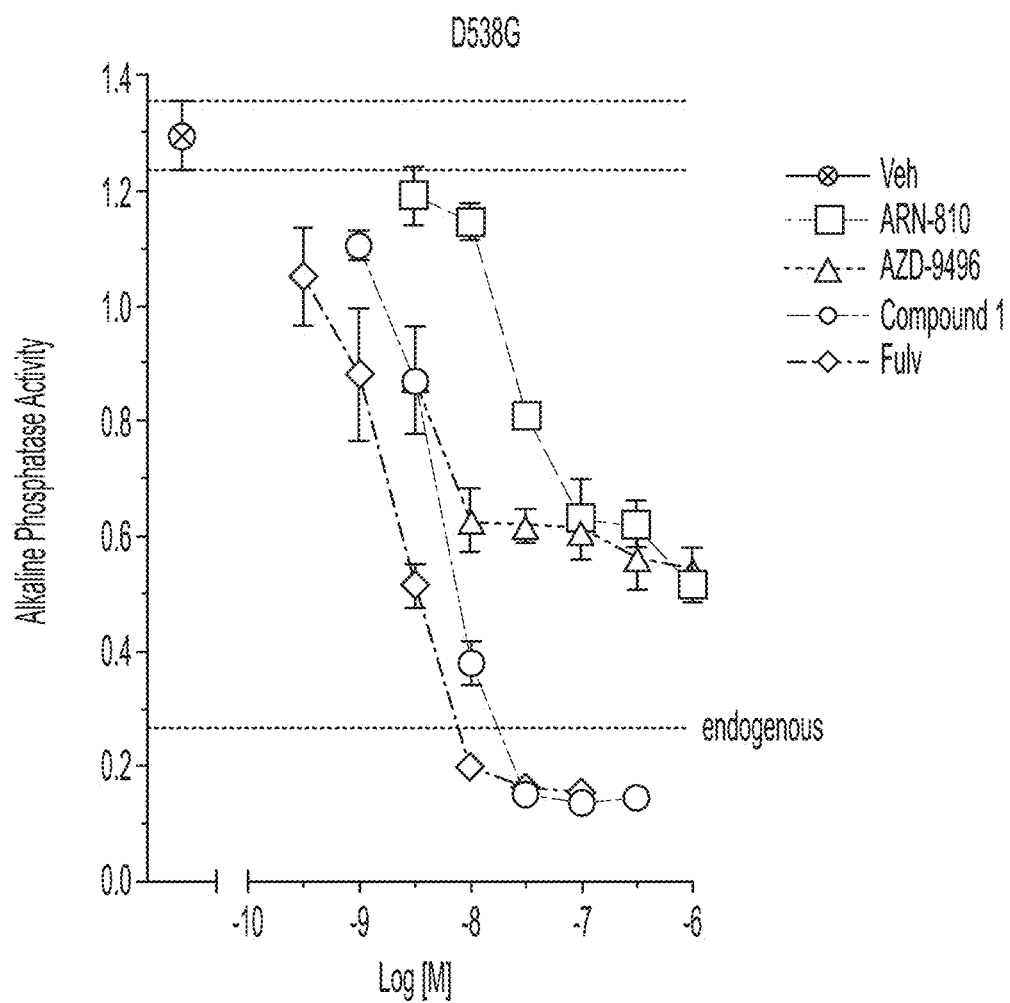
Figure 8D:
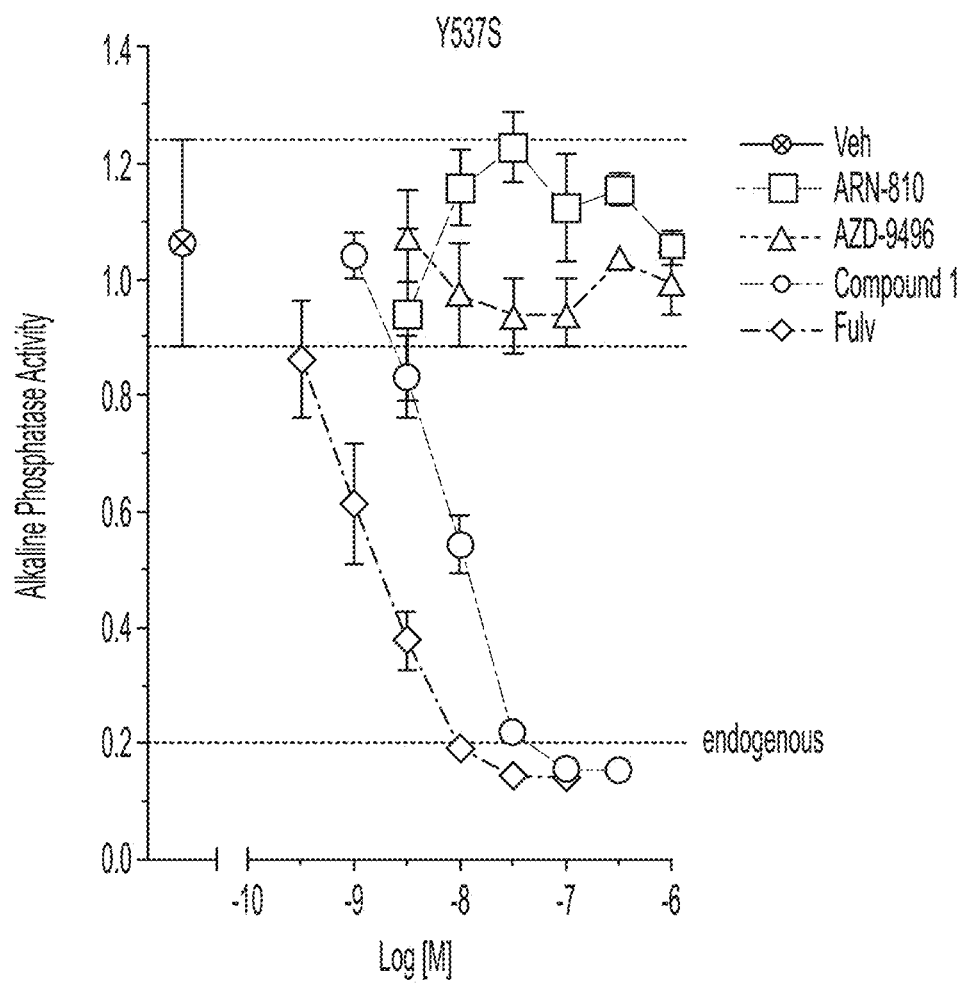

Certain Clinical Candidates Fail to Inhibit Activity of Ligand-Independent ER Mutants Wild type ER or an indicated ER variant transiently transfected into Ishikawa cells as described above, and activity was assayed in the presence of Compound 1 or Fulvestrant, as compared with Endoxifen, RAD-1901, ARN-810 (GDC-0810) or AZD-9496 (Results are depicted in FIGS. 8A-8B, where Compound 1 and Fulvestrant are compared with Endoxifen and RAD-1901 in FIGS. 8A and 8B, or with ARN-810 (GDC-0810) and AZD-9496 in FIGS. 8C-8D. Points represent mean absorbance at 405 nm from triplicate wells, +s.e.m. Line represents AP activity of the endogenous receptor (transfected with empty vector (pSG5)). As can be seen, none of Endoxifen, RAD-1901, ARN-810 (GDC-0810) or AZD-9496 can inhibit activity of the ligand-independent ER variants as Compound 1 and Fulvestrant do.

The invention claimed is:

1. A method of treating a subject suffering from a cancer characterized by a mutation of Estrogen Receptor 1 (ESR1), the method comprising administering to the subject Compound 1:

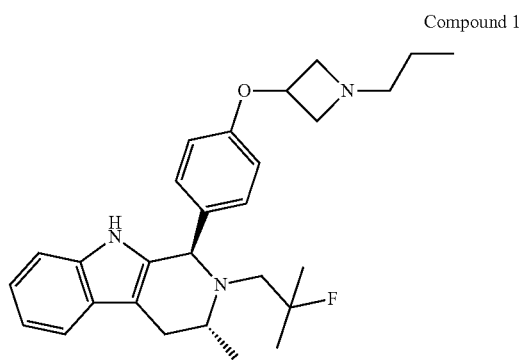 [SMILES: CCCN1CC(Oc2ccc([C@@H]3c4[nH]c5ccccc5c4C[C@@H](C)N3CC(C)(C)F)cc2)C1]

Compound 1 or a pharmaceutically acceptable salt thereof, wherein the mutation is an activation mutation, wherein the activation mutation is D538G or Y537S.

2. The method of claim 1, wherein the subject is receiving or has received a secondary agent and the secondary agent is a CDK4/6 inhibitor.

3. The method of claim 2, wherein the CDK4/6 inhibitor is selected from palbociclib, ribociclib, abemaciclib, lerociclib, and trilaciclib.

4. The method of claim 3, wherein the CDK4/6 inhibitor is palbociclib.

5. The method of claim 1, wherein the subject is receiving or has received a secondary agent and the secondary agent is a PIK3CA inhibitor.

6. The method of claim 5, wherein the PIK3CA inhibitor is selected from alpelisib and taselisib.

7. The method of claim 1, wherein the subject is receiving or has received a secondary agent and the secondary agent is an mTOR inhibitor.

8. The method of claim 7, wherein the mTOR inhibitor is selected from sirolimus, temsirolimus, and everolimus.

9. The method of claim 1, wherein the activation mutation is D538G.

10. The method of claim 1, wherein the activation mutation is Y537S.

* * * * *